(12) United States Patent
Abouabdellah et al.

(10) Patent No.: US 8,114,866 B2
(45) Date of Patent: Feb. 14, 2012

(54) DERIVATIVES OF 1-PIPERAZINE- AND 1-HOMOPIPERAZINE-CARBOXYLATES, PREPARATION METHOD THEREOF AND USE OF SAME AS INHIBITORS OF THE FAAH ENZYME

(75) Inventors: Ahmed Abouabdellah, Vigneux (FR); Antonio Almario Garcia, Chatenay Malabry (FR); Christian Hoornaert, Antony (FR); Adrien Tak Li, Fontenay Aux Roses (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 12/701,897

(22) Filed: Feb. 8, 2010

(65) Prior Publication Data

US 2010/0137329 A1    Jun. 3, 2010

Related U.S. Application Data

(60) Division of application No. 11/473,284, filed on Jun. 22, 2006, now Pat. No. 7,687,503, which is a continuation of application No. PCT/FR2004/003289, filed on Dec. 17, 2004.

(30) Foreign Application Priority Data

Dec. 23, 2003   (FR) ...................... 03 15248

(51) Int. Cl.
*A61P 1/08*   (2006.01)
*A61P 9/00*   (2006.01)
*A61K 31/55*  (2006.01)
*C07D 243/08* (2006.01)

(52) U.S. Cl. ....................... 514/218; 540/575

(58) Field of Classification Search ................ 514/218; 540/575

See application file for complete search history.

(56) References Cited

FOREIGN PATENT DOCUMENTS

| EP | 0548798 | 6/1993 |
|----|---------|--------|
| WO | WO 97/14689 | 4/1997 |
| WO | WO 01/72728 | 10/2001 |
| WO | WO 03/097573 | 11/2003 |
| WO | WO 2004/099176 | 11/2004 |

*Primary Examiner* — Brenda Coleman
(74) *Attorney, Agent, or Firm* — Kelly L. Bender

(57) ABSTRACT

The invention relates to a compound having general formula (I):

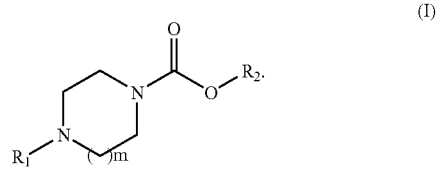

Wherein m, $R_1$ and $R_2$ are as defined herein. The invention also relates to the use of the compound in therapeutics. More specifically, the compounds of the invention are inhibitors of the FAAH enzyme, and therefore, can be used for the treatment of various disorders associated with FAAH enzyme, which include in a non-limiting manner, pain, eating disorders, neurological and psychiatric pathologies, among other disorders.

18 Claims, No Drawings

DERIVATIVES OF 1-PIPERAZINE- AND 1-HOMOPIPERAZINE-CARBOXYLATES, PREPARATION METHOD THEREOF AND USE OF SAME AS INHIBITORS OF THE FAAH ENZYME

CROSS REFERENCE TO RELATED APPLICATIONS

This application is a divisional of U.S. application Ser. No. 11/473,284, filed Jun. 22, 2006, now allowed, which is a continuation of International application No. PCT/FR2004/003,289, filed Dec. 17, 2004, both of which are incorporated herein by reference in their entirety; which claims the benefit of priority of French Patent Application No. 03/15248, filed Dec. 23, 2003

BACKGROUND OF THE INVENTION

Field of the Invention

The invention relates to 1-piperazine- and 1-homopiperazine-carboxylate derivatives, and to the preparation and therapeutic application thereof.

SUMMARY OF THE INVENTION

The compounds of the invention correspond to the general formula (I)

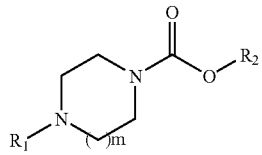

(I)

in which m represents an integer equal to 1 or 2;

$R_1$ represents a group chosen especially from a phenyl, pyridyl, pyridazinyl, pyrimidinyl, pyrazinyl, triazinyl, oxazolyl, triazolyl, imidazolyl, oxadiazolyl, thiadiazolyl, triazolyl, naphthyl, quinolyl, tetrahydroquinolyl, isoquinolyl, tetrahydroisoquinolyl, phthalazinyl, quinazolinyl, quinoxalinyl, cinnolinyl, naphthyridinyl, benzofuryl, dihydrobenzofuryl, benzothienyl, dihydrobenzothienyl, indolyl, benzoxazolyl, benzisoxazolyl, benzothiazolyl, benzisothiazolyl, benzimidazolyl, indazolyl, pyrrolopyridyl, furopyridyl, dihydrofuropyridyl, thienopyridyl, dihydrothienopyridyl, imidazopyridyl, imidazopyrimidinyl, pyrazolopyridyl, oxazolopyridyl, isoxazolopyridyl, thiazolopyridyl or isothiazolopyridyl, this group being optionally substituted with one or more groups $R_3$, which may be identical or different, or with a group $R_4$;

$R_2$ represents a group of general formula $CHR_5CONHR_6$, $R_3$ represents a halogen atom or a hydroxyl, cyano, nitro, $C_{1-6}$-alkyl, $C_{1-6}$-alkoxy, $C_{1-6}$-thioalkyl, $C_{1-6}$-fluoroalkyl, $C_{1-6}$-fluoroalkoxy, —O—($C_{2-3}$-alkylene)-, —O—($C_{1-3}$-alkylene)-O—, $C_{1-6}$-fluorothioalkyl, $C_{3-7}$-cycloalkyl, $C_{3-7}$-cycloalkyl-$C_{1-3}$-alkylene, piperidyl, benzyloxy, piperazinyl, pyrrolidinyl, morpholinyl, phenyloxy, $NR_7R_8$, $NHCOR_7$, $NHSO_2R_7$, $COR_7$, $CO_2R_7$, $CONR_7R_8$, $SO_2R_7$ or $SO_2NR_7R_8$ group, $R_4$ represents a group chosen especially from a phenyl, benzofuryl, naphthyl, pyridyl, pyrimidinyl, pyridazinyl, pyrazinyl, triazinyl, oxazolyl, thiazolyl, imidazolyl, oxadiazolyl, thiadiazolyl, triazolyl, quinolyl, tetrahydroquinolyl, isoquinolyl, tetrahydroisoquinolyl, phthalazinyl, quinazolinyl, quinoxalinyl, naphthyridinyl, cinnolinyl, imidazolpyrimidinyl, benzothienyl, indolyl, benzoxazolyl, benzisoxazolyl, benzothiazolyl, benzisothiazolyl, benzimidazolyl, indazolyl, pyrrolopyridyl, furopyridyl, dihydrofuropyridyl, thienopyridyl, dihydrothienopyridyl, imidazopyridyl, imidazopyrimidinyl, pyrazopyridyl, oxazolopyridyl, isoxazolopyridyl, thiazolopyridyl or isothiazolopyridyl;

the group(s) $R_4$ possibly being substituted with one or more groups $R_3$, which may be identical or different, $R_5$ represents a hydrogen atom or a $C_{1-3}$-alkyl group;

$R_6$ represents a hydrogen atom or a $C_{1-6}$-alkyl, $C_{3-7}$-cycloalkyl or $C_{3-7}$-cycloalkyl-$C_{1-3}$-alkylene group;

$R_7$ and $R_8$ represent, independently of each other, a hydrogen atom, a $C_{1-3}$-alkyl group or a phenyl group.

DETAILED DESCRIPTION OF THE INVENTION

Among the compounds of general formula (I), a first sub-group of compounds consists of compounds for which:

m represents an integer equal to 1 or 2; and/or $R_1$ represents a group chosen especially from a phenyl, pyridyl, pyrimidinyl, pyrazinyl, naphthyl, quinolyl, isoquinolyl, benzisoxazolyl, thienopyridyl, this group being optionally substituted with one or more groups $R_3$, more particularly with one or two groups $R_3$, which may be identical or different; and/or $R_2$ represents a group of general formula $CHR_5CONHR_6$; and/or $R_3$ represents a halogen atom, more particularly a chlorine, a bromine or a fluorine, or a cyano group, $C_{1-6}$-alkyl, more particularly a methyl, ethyl, n-propyl or isobutyl, $C_{1-6}$-alkoxy, more particularly a methoxy, $C_{1-6}$-fluoroalkyl, more particularly a $CF_3$, $C_{1-6}$-fluoroalkoxy, more particularly an —OCH$_2$CF$_3$, —O—($C_{2-3}$-alkylene)-, more particularly an —O—(CH$_2$)$_3$—, phenyloxy; and/or $R_5$ represents a hydrogen atom; and/or $R_6$ represents a hydrogen atom or a $C_{1-6}$-alkyl group, more particularly a methyl.

Among the compounds of general formula (I), a second sub-group of compounds consists of compounds for which:

m is equal to 1; and/or $R_1$ represents a group chosen especially from a pyridyl, pyrimidinyl, pyrazinyl, quinolyl and isoquinolyl, this group being optionally substituted with a group $R_3$; and/or $R_2$ represents a group of general formula $CHR_5CONHR_6$; and/or $R_3$ represents a halogen atom, more particularly a chlorine, or a $C_{1-6}$-alkyl group, more particularly a methyl, ethyl, n-propyl or isobutyl, $C_{1-6}$-alkoxy, more particularly a methoxy, $C_{1-6}$-fluoroalkyl, more particularly a $CF_3$; and/or $R_5$ represents a hydrogen atom; and/or $R_6$ represents a hydrogen atom or a $C_{1-6}$-alkyl group, more particularly a methyl.

Among the compounds of general formula (I), a third sub-group of compounds consists of compounds for which:

m represents an integer equal to 1 or 2; and/or $R_1$ represents a group chosen especially from a phenyl, pyridyl, pyridazinyl, pyrimidinyl and thiadiazolyl, this group being optionally substituted with a group $R_4$; and/or $R_4$ represents a group chosen especially from a phenyl, benzofuryl and naphthyl; the group $R_4$ possibly being substituted with one or more groups $R_3$, which may be identical or different, more particularly with one or two groups $R_3$, which may be identical or different; and/or $R_2$ represents a group of general formula $CHR_5CONHR_6$; and/or $R_3$ represents a halogen atom, more particularly a chlorine, a bromine or a fluorine, or a nitro group, $C_{1-6}$-alkyl, more particularly a methyl, isopropyl, $C_{1-6}$-alkoxy, more particularly a methoxy, ethoxy, $C_{1-6}$-fluoroalkyl, more particularly a $CF_3$, $C_{1-6}$-fluoroalkoxy, more particularly a $OCF_3$, —O—($C_{1-3}$-alkylene)-O—, more particularly an —O—$CH_2$—O—, benzyloxy; and/or $R_5$ represents a hydrogen atom; and/or $R_6$ represents a hydrogen atom or a $C_{1-6}$-alkyl group, more particularly a methyl or an ethyl, or $C_{3-7}$-cycloalkyl-$C_{1-3}$-alkylene, more particularly a cyclopropyl-$CH_2$—.

Among the compounds of general formula (I), a fourth sub-group of compounds consists of compounds for which:

m is equal to 1; and/or $R_1$ represents a group chosen especially from a phenyl, pyridyl, pyridazinyl and pyrimidinyl, this group being optionally substituted with a group $R_4$; and/or $R_4$ represents a group chosen especially from a phenyl, benzofuryl and naphthyl; the group $R_4$ possibly being substituted with one or more groups $R_3$, which may be identical or different, more particularly with one or two groups $R_3$, which may be identical or different; and/or $R_2$ represents a group of general formula $CHR_5CONHR_6$; and/or $R_3$ represents a halogen atom, more particularly a chlorine, a bromine or a fluorine, or a nitro group, $C_{1-6}$-alkyl, more particularly a methyl, isopropyl, $C_{1-6}$-alkoxy, more particularly a methoxy, ethoxy, $C_{1-6}$-fluoroalkyl, more particularly a $CF_3$, $C_{1-6}$-fluoroalkoxy, more particularly an $OCF_3$, —O—($C_{1-3}$-alkylene)-O—, more particularly an —O—$CH_2$—O—, benzyloxy; and/or $R_5$ represents a hydrogen atom; and/or $R_6$ represents a hydrogen atom or a $C_{1-6}$-alkyl group, more particularly a methyl or an ethyl.

The compounds of general formula (I) may comprise one or more asymmetric carbons. They may exist in the form of enantiomers and/or diastereoisomers. These enantiomers and diastereoisomers, and also mixtures thereof, including racemic mixtures thereof, form part of the invention.

The compounds of formula (I) may exist in the form of bases or of acid-addition salts. Such addition salts form part of the invention.

These salts are advantageously prepared with pharmaceutically acceptable acids, but the salts of other acids that are useful, for example for the purification or isolation of the compounds of formula (I), also form part of the invention.

The compounds of general formula (I) may be in the form of hydrates or of solvates, i.e. in the form of associations or combinations with one or more water molecules or with a solvent. Such hydrates and solvates also form part of the invention.

In the context of the invention, the following definitions apply:

$C_{t-z}$ in which t and z may take the values from 1 to 7, a carbon-based chain possibly containing from t to z carbon atoms, for example $C_{1-3}$ is a carbon-based chain which may contain from 1 to 3 carbon atoms, alkyl, a saturated, linear or branched aliphatic group, for example a $C_{1-3}$-alkyl group represents a linear or branched carbon-based chain of 1 to 3 carbon atoms, more particularly a methyl, ethyl, propyl or 1-methylethyl, alkylene, a saturated, linear or branched divalent alkyl group, for example a $C_{1-3}$-alkylene group represents a linear or branched divalent carbon-based chain of 1 to 3 carbon atoms, more particularly a methylene, ethylene, 1-methylethylene or propylene, cycloalkyl, a cyclic alkyl group, for example a $C_{3-5}$-cycloalkyl group represents a cyclic carbon-based group of 3 to 5 carbon atoms, more particularly a cyclopropyl, cyclobutyl or cyclopentyl, alkoxy, an —O-alkyl group containing a saturated, linear or branched aliphatic chain, thioalkyl, an —S-alkyl group containing a saturated, linear or branched aliphatic chain, fluoroalkyl, an alkyl group in which one or more hydrogen atoms have been replaced with a fluorine atom, fluoroalkoxy, an alkoxy group in which one or more hydrogen atoms have been replaced with a fluorine atom, fluorothioalkyl, a thioalkyl group in which one or more hydrogen atoms have been replaced with a fluorine atom halogen atom, a fluorine, a chlorine, a bromine or an iodine.

The compounds of the invention may be prepared according to various methods, illustrated by the schemes that follow.

Thus, a first preparation method (scheme 1) consists in reacting an amine of general formula (II), in which $R_1$ and m are as defined in the general formula (I), with a carbonate of general formula (III), in which Z represents a hydrogen atom or a nitro group and $R_2$ is as defined in the general formula (I), in a solvent such as toluene or dichloroethane, at a temperature of between 0 and 80° C.

Scheme 1

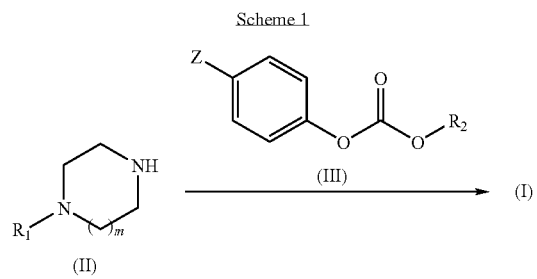

The carbonates of general formula (III) may be prepared according to any method described in the literature, for example by reacting an alcohol of general formula $HOR_2$ with phenyl chloroformate or 4-nitrophenyl chloroformate, in the presence of a base such as triethylamine or diisopropylethylamine, at a temperature of between 0° C. and the reflux temperature of the solvent.

According to a second method (scheme 2), the compounds of general formula (I) may be prepared by reacting an amine of general formula (II), as defined above, with a carbonate of general formula (IIIa) in which Z represents a hydrogen atom or a nitro group, $R_5$ is as defined in the general formula (I) and R represents a methyl or ethyl group. The carbamate-ester of general formula (Ia) thus obtained is then converted into a compound of general formula (I), via aminolysis using an amine of general formula $R_6NH_2$ in which $R_6$ is as defined in the general formula (I). The aminolysis reaction may be performed in a solvent such as methanol or a mixture of solvents such as methanol and tetrahydrofuran or methanol and dioxane.

Scheme 2

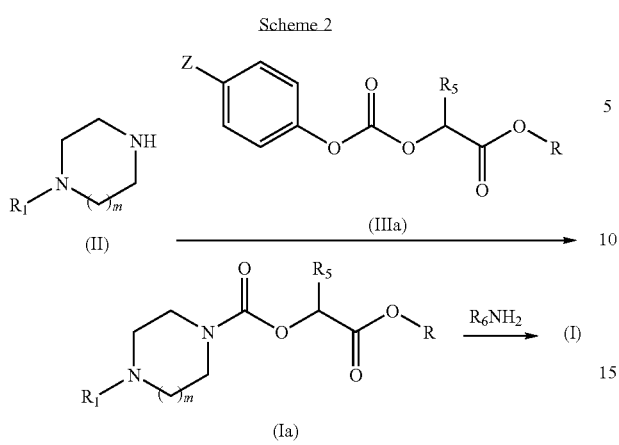

The carbonates of general formula (IIIa) may be prepared according to any method described in the literature, for example by reacting an alcohol of general formula HOCHR$_5$COOR in which R represents a methyl or ethyl group, with phenyl chloroformate or 4-nitrophenyl chloroformate, in the presence of a base such as triethylamine or diisopropylethylamine.

The compounds of general formula (I), in which $R_1$ represents a group substituted with a group $R_3$ of $C_{1-6}$-alkyl, $C_{3-7}$-cycloalkyl or $C_{3-7}$-cycloalkyl-$C_{1-3}$-alkylene type, or with a group $R_4$ as defined in the general formula (I), may also be prepared via a Suzuki reaction performed on the corresponding compounds of general formula (I), for which $R_1$ is substituted with a chlorine, bromine or iodine atom or with a triflate group at the position in which the group $R_3$ or $R_4$ is to be introduced, for example using an alkyl, cycloalkyl, aryl or heteroaryl boronic acid.

For the compounds of general formula (I), in which $R_1$ represents a group substituted with a group $R_3$ of $C_{1-6}$-alkyl, $C_{3-7}$-cycloalkyl or $C_{3-7}$-cycloalkyl-$C_{1-3}$-alkylene type or with a group $R_4$ as defined in the general formula (I), and $R_2$ more particularly represents a group of general formula CHR$_5$CONHR$_6$, the Suzuki reaction described above may be performed on the carbamate-ester of general formula (Ia) as defined above. The action of an amine of general formula $R_6NH_2$ as defined above on the carbamate-ester thus obtained makes it possible to obtain the compounds of general formula (I).

The compounds of general formula (II), when their mode of preparation is not described, are commercially available or described in the literature, or may even be prepared according to methods that are described therein or that are known to those skilled in the art.

The amines of general formula $R_6NH_2$ are commercially available.

According to another of its aspects, a subject of the invention is also the compounds of formula (Ia). These compounds are useful as intermediates for synthesizing the compounds of formula (I).

The examples that follow illustrate the preparation of a number of compounds of the invention. These examples are not limiting and serve merely to illustrate the invention. The microanalyses and the IR and NMR and/or LC-MS (Liquid Chromatography coupled to Mass Spectroscopy) spectra confirm the structures and the purities of the compounds obtained.

m.p. (° C.) represents the melting point in degrees Celsius. The numbers indicated in parentheses in the example titles correspond to those in the first column of the table below:

EXAMPLE 1

Compound 44

2-(methylamino)-2-oxoethyl 4-{4'-[(trifluoromethyl)oxy]-4-biphenyl}-1-piperazinecarboxylate

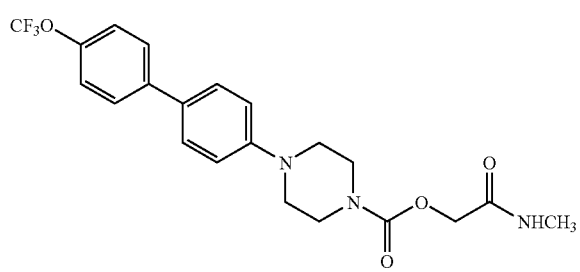

1.1. ethyl [(phenyloxycarbonyl)oxy]acetate 32 ml (256 mmol) of phenyl chloroformate are added slowly at room temperature to a solution of 25 g (240 mmol) of ethyl glycolate and 55 ml (315 mmol) of diisopropylethylamine in 500 ml of toluene. Stirring is continued at room temperature for 2 hours. The salt formed is separated out and the filtrate is concentrated under reduced pressure. 53.7 g of oily product are obtained, and are used without further purification in the following step.

1.2. 2-(ethyloxy)-2-oxoethyl 4-(4-bromophenyl)-1-piperazinecarboxylate

A solution of 5.81 g (24.08 mmol) of 1-(4-bromophenyl)piperazine and 6 g (26.76 mmol) of ethyl [(phenyloxycarbonyl)oxy]acetate, obtained in step 1.1, in 50 ml of toluene, is heated at 80° C. for 12 hours.

The mixture is allowed to cool to room temperature, it is concentrated under reduced pressure and the residue thus obtained is then purified by chromatography on silica gel, eluting with a 20/80 and then 30/70 mixture of ethyl acetate and cyclohexane. 7.75 g of pure product in the form of an oil that crystallizes at room temperature are thus obtained.

m.p. (° C.): 80-82° C.

1.3. 2-(ethyloxy)-2-oxoethyl 4-{4'-(trifluoromethyl)oxy]-4-biphenylyl}-1-piperazinecarboxylate 2 g (5.39 mmol) of 2-(ethyloxy)-2-oxoethyl 4-(4-bromophenyl)-1-piperazinecarboxylate, obtained in step 1.2, 3.33 g (16.16 mmol) of 4-(trifluoromethoxy)phenylboronic acid and 4.57 g (21.55 mmol) of hydrated potassium phosphate suspended in 18 ml of 1,2-dimethoxyethane are introduced, under an inert atmosphere. 0.62 g (0.54 mmol) of tetrakis(triphenylphosphine)palladium is then added. The reaction mixture is then maintained at about 80° C. for 12 hours. It is concentrated under reduced pressure. The residue is taken up with dichloromethane and water, the aqueous phase is separated out and extracted twice with dichloromethane, the combined organic phases are dried over sodium sulfate and the filtrate is concentrated under reduced pressure. The residue thus obtained is purified by chromatography on silica gel, eluting with a 30/70 mixture of ethyl acetate and cyclohexane. 1.65 g of product are obtained in the form of a white solid.

m.p. (° C.): 112-116° C.

1.4. 2-(methylamino)-2-oxoethyl 4-{4'-[(trifluoromethyl)oxy]-4-biphenylyl}-1-piperazinecarboxylate 7.10 ml (14.15 mmol) of a solution of methylamine (2M) in tetrahydrofuran are added to a solution of 1.60 g (3.54 mmol) of 2-(ethyloxy)-2-oxoethyl 4-{4'-[(trifluoromethyl)oxy]-4-biphenylyl}-1-piperazinecarboxylate, prepared in step 1.3, in 14 ml of methanol. Stirring is continued at room temperature for 12 hours. After concentrating under reduced pressure, the residue obtained is purified by chromatography on silica gel, eluting with a 97/3 mixture of dichloromethane and methanol. A solid is obtained, and is recrystallized from a mixture of ethyl acetate and diisopropyl ether. 0.86 g of pure product is thus obtained in the form of a white solid.

LC-MS: M+H=438 m.p. (° C.): 187-189° C.

$^1$H NMR (CDCl$_3$) δ (ppm): 2.90 (d, 3H); 3.25 (m, 4H); 3.70 (m, 4H); 4.60 (s, 2H); 6.10 (broad s, 1H); 7.0 (d, 2H); 7.30 (d, 2H); 7.50 (d, 2H); 7.60 (d, 2H).

EXAMPLE 2

Compound 37

2-(methylamino)-2-oxoethyl 4-[3'-(trifluoromethyl)-4-biphenylyl]-1-piperazinecarboxylate

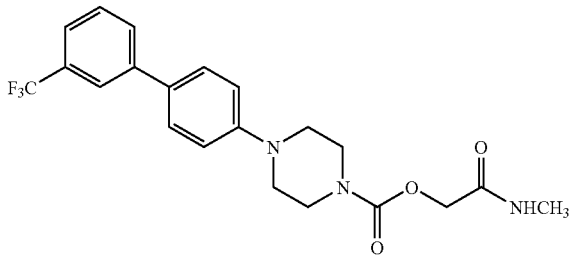

2.1. 2-(methylamino)-2-oxoethyl 4-nitrophenyl carbonate 5.93 g (29.4 mmol) of 4-nitrophenyl chloroformate are added portionwise and at room temperature to a suspension of 2.62 g (29.4 mmol) of 2-hydroxy-N-methylacetamide and 16.5 g (58.7 mmol) of supported diisopropylethylamine (Ps-DIEA from Argonaut, charge=3.56 mmol/g) in 250 ml of dichloromethane. Orbital stirring is continued at room temperature for 16 hours. The resin is filtered off and rinsed with 150 ml of dichloromethane, and the filtrate is concentrated under reduced pressure. 6 g of product are obtained in the form of a pale yellow solid (purity estimated at 70%), and are used without further purification in the following step.

2.2. 2-(methylamino)-2-oxoethyl 4-(4-bromophenyl)-1-piperazinecarboxylate 1.17 g (4.85 mmol) of 1-(4-bromophenyl)piperazine are added to a solution of 1.47 g (4 mmol) of 2-(methylamino)-2-oxoethyl 4-nitrophenyl carbonate, obtained in step 2.1, in 18 ml of 1,2-dichloroethane. This reaction mixture is heated at 65° C. for 2.25 hours. The mixture is allowed to cool to room temperature and it is then concentrated under reduced pressure. The oily yellow residue is taken up in dichloromethane and washed successively with sodium hydroxide (1N), water, aqueous 5% citric acid solution, water and then brine. This organic phase is dried over sodium sulfate and is concentrated under reduced pressure. After washing with diisopropyl ether, 1.3 g of product are obtained in the form of a white solid.

2.3. Synthesis of the Palladium Catalyst Grafted onto Merrifield Resin 54.6 ml (27.3 mmol) of a solution of lithium diphenylphosphide, sold at 0.5 M in THF under an inert atmosphere, are introduced into a suspension of 5 g (3.5 mmol) of Merrifield resin (Fluka, 200-400 Mesh, crosslinked with 2% of divinylbenzene (DVB), Charge=0.7 mmol/g) in 50 ml of anhydrous tetrahydrofuran (THF). Orbital stirring is continued at room temperature for 24 hours, and 60 ml of acetone and 20 ml of water are then added. The resin is filtered off and is washed successively with water, acetone, THF, a THF/H$_2$O (2/1) mixture, THF, toluene, dichloromethane and ethyl ether and is then dried under vacuum for 2 hours. A suspension of the resin thus obtained is maintained at 70° C. for 24 hours in 47 ml of ethanol and 23 ml of toluene. After filtration, the resin is washed successively with acetone, THF and ethyl ether. In total, this treatment is repeated four times to remove the soluble fractions of the polymer. The resin thus obtained is dried under vacuum for 2 hours. 0.18 g (0.16 mmol) of tetrakis(triphenylphosphine)palladium is added to a suspension of this resin in 60 ml of toluene and this reaction mixture is maintained at 95° C. for 24 hours. The mixture is allowed to cool to room temperature, and the resin is filtered off and washed successively with acetone, THF and then ethyl ether. 5.135 g of resin are obtained, and are used without further purification in the following step.

2.4. 2-(methylamino)-2-oxoethyl 4-[3'-(trifluoromethyl)-4-biphenylyl]-1-piperazinecarboxylate 0.18 g (0.5 mmol) of 2-(methylamino)-2-oxoethyl 4-(4-bromophenyl)-1-piperazinecarboxylate, obtained in step 2.2, 0.21 g (1.1 mmol) of 3-(trifluoromethyl)phenylboronic acid and 0.16 g (1.5 mmol) of sodium carbonate suspended in 3 ml of toluene and 0.3 ml of ethanol are introduced. 0.14 g (~10 mol %) of supported palladium catalyst, obtained in step 2.3, are then added and orbital stirring is continued at 80° C. for 48 hours. The mixture is allowed to cool to room temperature, the resin is filtered off and rinsed with dichloromethane, and the filtrate is concentrated under reduced pressure. The residue is taken up in 5 ml of dichloromethane and washed with water and then with saturated aqueous sodium bicarbonate solution. The organic phase is filtered through a hydrophobic cartridge and the filtrate is then concentrated under reduced pressure. An oily residue that crystallizes from diisopropyl ether is obtained. 0.15 g of white crystals is obtained.

LC-MS: M+H=422 m.p. (° C.): 129-130° C.

$^1$H NMR (CDCl$_3$) δ (ppm): 2.95 (d, 3H); 3.20-3.35 (m, 4H); 3.65-3.80 (m, 4H); 4.65 (s, 2H); 6.05 (broad s, 1H); 7.05 (d, 2H); 7.50-7.60 (m, 4H); 7.65-7.80 (m, 2H)

EXAMPLE 3

Compound 76

2-(methylamino)-2-oxoethyl 4-{5-[3-(trifluoromethyl)phenyl]-2-pyridyl}-1-piperazinecarboxylate

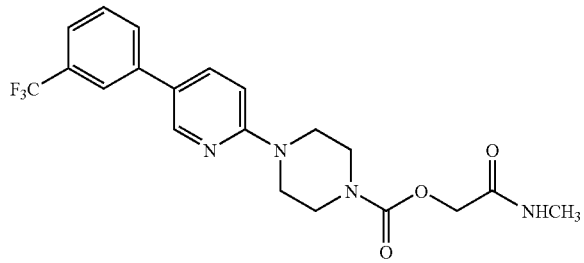

3.1. 1,1-dimethylethyl 4-(5-bromo-2-pyridyl)-1-piperazinecarboxylate 29.2 g (157 mmol) of 1,1-dimethylethyl 1-piperazinecarboxylate, 37 g (157 mmol) of 2,5-dibromopyridine and 21.7 g (157 mmol) of potassium carbonate suspended in 27 ml of dimethyl sulfoxide (DMSO) are introduced into an autoclave. The mixture is then heated at 150° C. for 21 hours. The reaction mixture is allowed to cool to room temperature, it is taken up in ethyl acetate and water and the insoluble material is then separated out by filtration. The aqueous phase is separated out and extracted twice with ethyl acetate, the combined organic phases are washed with saturated aqueous sodium chloride solution and dried over sodium sulfate, and the filtrate is concentrated under reduced pressure. The residue obtained is purified by chromatography on silica gel, eluting with a 99/1 mixture of dichloromethane and methanol. 44 g of product are thus obtained in the form of a white solid.

m.p. (° C.): 83-85° C.

3.2. 1-(5-bromo-2-pyridyl)piperazine 49 ml (272 mmol) of a solution of hydrochloric acid (6N) in isopropanol are added at room temperature to a solution of 18.60 g (54.40 mmol) of 1,1-dimethylethyl 4-(5-bromo-2-pyridyl)-1-piperazinecarboxylate, obtained in step 3.1, in 100 ml of 1,4-dioxane. The reaction mixture is then maintained at about 60° C. for 3 hours. The mixture is concentrated to dryness under reduced pressure. The dihydrochloride obtained is taken up in 200 ml of dichloromethane and 200 ml of water, followed by portionwise addition, with stirring, of 10 g of sodium hydrogen carbonate. The phases are separated by settling, the aqueous phase is extracted twice with dichloromethane, and the combined organic phases are washed with saturated aqueous sodium chloride solution, dried over sodium sulfate and concentrated under reduced pressure. 12 g of product are obtained in the form of a white solid.

m.p. (° C.): 72° C.

3.3. 2-(ethyloxy)-2-oxoethyl 4-(5-bromo-2-pyridyl)-1-piperazinecarboxylate

The process is performed as described in Example 1 (step 1.2.). Starting with 6 g (24.80 mmol) of 1-(5-bromo-2-pyridyl)piperazine, obtained in step 3.2, and 10.88 g (48.52 mmol) of ethyl [(phenyloxycarbonyl)oxy]acetate, prepared in step 1.1. of Example 1, and after chromatography on silica gel, eluting with a 15/85 and then 30/70 mixture of ethyl acetate and cyclohexane, 6.70 g of product are obtained in the form of an oil that crystallizes to a white solid.

3.4. 2-(ethyloxy)-2-oxoethyl 4-{5-[3-(trifluoromethyl)phenyl]-2-pyridyl}-1-piperazinecarboxylate The process is performed according to the procedure described in Example 1 (step 1.3.). Starting with 3 g (8.06 mmol) of 2-(ethyloxy)-2-oxoethyl 4-(5-bromo-2-pyridyl)-1-piperazinecarboxylate, obtained in step 3.3, 4.59 g (24.17 mmol) of 3-(trifluoromethyl)phenylboronic acid, 6.84 g (32.23 mmol) of hydrated potassium phosphate and 0.93 g (0.806 mmol) of tetrakis(triphenylphosphine)palladium, and after chromatography on silica gel, eluting with a 30/70 mixture of ethyl acetate and cyclohexane, 2.22 g of product are obtained in the form of a white solid.

3.5. 2-(methylamino)-2-oxoethyl 4-{5-[3-(trifluoromethyl)phenyl]-2-pyridyl}-1-piperazinecarboxylate The process is performed according to the procedure described in Example 1 (step 1.4.). Starting with 1.50 g (3.43 mmol) of 2-(ethyloxy)-2-oxoethyl 4-{5-[3-(trifluoromethyl)phenyl]-2-pyridyl}-1-piperazinecarboxylate, obtained in step 3.4, and 8.6 ml (17.15 mmol) of a solution of methylamine (2M) in tetrahydrofuran, and after chromatography on silica gel, eluting with a 97/3 mixture of dichloromethane and methanol, followed by washing with diisopropyl ether, 1.18 g of product are obtained in the form of a white solid.

LC-MS: M+H=423 m.p. (° C.): 158-160° C.

$^1$H NMR (CDCl$_3$) δ (ppm): 2.90 (d, 3H); 3.75 (broad s, 8H); 4.65 (s, 2H); 6.05 (broad s, 1H); 6.75 (d, 1H); 7.50-7.80 (multiplet, 5H); 8.50 (d, 1H).

EXAMPLE 4

Compound 79

2-(methylamino)-2-oxoethyl 4-{5-[4-(trifluoromethyl)phenyl]-2-pyridyl}-1-piperazinecarboxylate

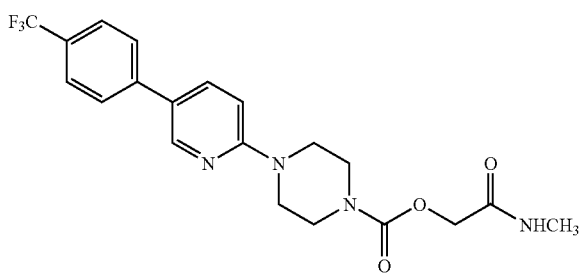

4.1. 2-(ethyloxy)-2-oxoethyl 4-{5-[4-(trifluoromethyl)phenyl]-2-pyridyl}-1-piperazinecarboxylate The process is performed according to the procedure described in Example 1 (step 1.3.). Starting with 4 g (10.75 mmol) of 2-(ethyloxy)-2-oxoethyl 4-(5-bromo-2-pyridyl)-1-piperazinecarboxylate, obtained in step 3.3. of Example 3, 5.50 g (28.96 mmol) of 4-(trifluoromethyl)phenylboronic acid, 9.12 g (42.99 mmol) of hydrated potassium phosphate and 1.24 g (1.07 mmol) of tetrakis(triphenylphosphine)palladium, and after chromatography on silica gel, eluting with a 30/70 mixture of ethyl acetate and cyclohexane, 2.78 g of product are obtained in the form of a white solid.

4.2. 2-(methylamino)-2-oxoethyl 4-{5-[4-(trifluoromethyl)phenyl]-2-pyridyl}-1-piperazinecarboxylate The process is performed according to the procedure described in Example 1 (step 1.4.). Starting with 2.77 g (6.33 mmol) of 2-(ethyloxy)-2-oxoethyl 4-{5-[4-(trifluoromethyl)phenyl]-2-pyridyl}-1-piperazinecarboxylate, obtained in step 4.1, and 15.80 ml (31.67 mmol) of a solution of methylamine (2M) in tetrahydrofuran, and after chromatography on silica gel, eluting with a 97/3 mixture of dichloromethane and methanol, followed by recrystallization from ethyl acetate, 1.69 g of product are obtained in the form of a white solid.

LC-MS: M+H=423
m.p. (° C.): 206-209° C.
$^1$H NMR (CDCl$_3$) δ (ppm): 2.90 (d, 3H); 3.70 (broad s, 8H); 4.65 (s, 2H); 6.05 (broad s, 1H); 6.75 (d, 1H); 7.60-7.75 (m, 4H); 7.80 (dd, 1H); 8.50 (d, 1H).

EXAMPLE 5

Compound 83

2-(methylamino)-2-oxoethyl 4-(5-{4-[(trifluoromethyl)oxy]phenyl}-2-pyridyl)-1-piperazinecarboxylate

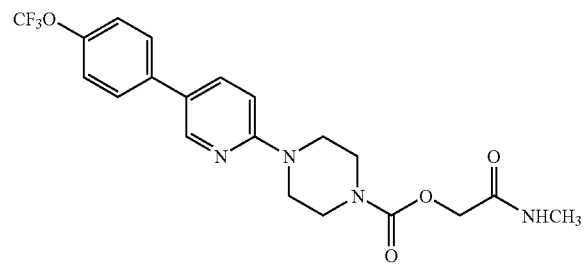

5.1. 1,1-dimethylethyl 2-(methylamino)-2-oxoethyl 1,4-piperazinedicarboxylate A solution of 0.53 g (2.85 mmol) of 1,1-dimethylethyl 1-piperazinecarboxylate in 5 ml of 1,2-dichloroethane is added dropwise at about 0° C. to a solution, cooled to 0° C., of 1.1 g (3 mmol) of 2-(methylamino)-2-oxoethyl 4-nitrophenyl carbonate, prepared in step 2.2. of Example 2, in 10 ml of 1,2-dichloroethane. Stirring is continued at 0° C. for 1 hour, and then at room temperature for 3 hours. The reaction mixture is concentrated under reduced pressure and the residue thus obtained is purified by chromatography on silica gel, eluting with a 20/80 mixture of ethyl acetate and cyclohexane. The gradient is gradually increased to complete the elution with ethyl acetate. An oily residue that crystallizes from diisopropyl ether is obtained. 0.61 g of product is obtained in the form of a white solid, and is used without further purification in the following step.

5.2. 2-(methylamino)-2-oxoethyl 1-piperazinecarboxylate hydrochloride 25 ml of a 6N solution of hydrogen chloride in isopropanol are added to a solution of 2.68 g (8.9 mmol) of 2-(methylamino)-2-oxoethyl 1,1-dimethylethyl-1,4-piperazinedicarboxylate, obtained according to step 5.1, in 25 ml of dichloromethane. Stirring is continued at room temperature for 1 hour. The organic phase is removed by filtration through a hydrophobic cartridge and the acidic aqueous phase is concentrated under reduced pressure. After crystallization from isopropanol, 2.05 g of product are obtained in the form of a white solid, and are used without further purification in the following step.

m.p. (° C.): 167-169° C.

5.3. 2-(methylamino)-2-oxoethyl 4-(5-nitro-2-pyridyl)-1-piperazinecarboxylate 1.84 g (11.6 mmol) of 2-chloro-5-nitropyridine are added to a solution of 2.05 g (8.62 mmol) of 2-(methylamino)-2-oxoethyl 1-piperazinecarboxylate hydrochloride, obtained in step 5.2, and 3.85 ml (22.4 mmol) of N,N diisopropylethylamine in 55 ml of 1,2-dichloroethane. This reaction mixture is maintained at 70° C. for 5 hours. The mixture is allowed to cool to room temperature and concentrated under reduced pressure, and the residue thus obtained is purified by chromatography on silica gel, eluting with a 98/2 mixture of dichloromethane and methanol. 2.48 g of product are obtained in the form of a pale yellow solid, and are used without further purification in the following step.

5.4. 2-(methylamino)-2-oxoethyl 4-(5-amino-2-pyridyl)-1-piperazinecarboxylate 0.24 g of 10% palladium on charcoal is added to a suspension of 0.64 g (1.98 mmol) of 2-(methylamino)-2-oxoethyl 4-(5-nitro-2-pyridyl)-1-piperazinecarboxylate, prepared in step 5.3, in 90 ml of ethyl acetate. Stirring is continued at room temperature under a hydrogen atmosphere of 60 psi for 14 hours. After filtering off the catalyst, the filtrate is concentrated under reduced pressure and the residue thus obtained is purified by chromatography on silica gel, eluting with a 98/2 mixture of dichloromethane and methanol. 0.47 g of product is obtained in the form of a violet-colored oil, and is used without further purification in the following step.

5.5. 2-(methylamino)-2-oxoethyl 4-(5-iodo-2-pyridyl)-1-piperazinecarboxylate A solution of 0.16 g (2.2 mmol) of sodium nitrite dissolved in 3.5 ml of water is slowly added to a solution, cooled to 0° C., of 0.47 g (1.5 mmol) of 2-(methylamino)-2-oxoethyl 4-(5-amino-2-pyridyl)-1-piperazinecarboxylate, prepared in step 5.4, in 15 ml of aqueous sulfuric acid solution (0.33N). Stirring is continued at about 0° C. for half an hour, and 0.83 g (5 mmol) of potassium iodide is slowly added. Stirring is continued at this temperature for half an hour and the reaction mixture is then maintained at 85° C. for 2 hours. After cooling to room temperature, the reaction medium is basified to pH=14, by adding saturated aqueous sodium bicarbonate solution. The aqueous phase is extracted three times with dichloromethane, the combined organic phases are washed with aqueous 35% thiosulfite solution, water, brine and dried over sodium sulfate. The filtrate is concentrated under reduced pressure and the residue thus obtained is purified by chromatography on silica gel, eluting with a 98/2 mixture of dichloromethane and methanol. After washing with diisopropyl ether, 0.35 g of product is obtained in the form of a beige-colored solid, and is used without further purification in the following step.

5.6. 2-(methylamino)-2-oxoethyl 4-(5-{4-[(trifluoromethyl)oxy]phenyl}-2-pyridyl)-1-piperazinecarboxylate The process is performed according to the procedure described in Example 2 (step 2.4.). Starting with 0.250 g (0.61 mmol) of 2-(methylamino)-2-oxoethyl 4-(5-iodo-2-pyridyl)-1-piperazinecarboxylate, obtained in step 5.5, 0.51 g (2.44 moles) of 4-(trifluoromethoxy)phenylboronic acid, 0.61 g (~8 mol %) of palladium catalyst on a solid support, prepared in step 2.1. of Example 2, and 2.9 ml (7.32 mmol) of aqueous sodium carbonate solution (2.5M) suspended in 12 ml of toluene and 3 ml of ethanol, and after chromatography on silica gel, eluting with a 98/2 mixture of dichloromethane and methanol, followed by washing with diisopropyl ether, 0.092 g of product is obtained in the form of a white solid.

LC-MS: M+H=439
m.p. (° C.): 188-190° C.
$^1$H NMR (CDCl$_3$) (ppm): 2.90 (d, 3H); 4.70 (broad s, 8H); 4.65 (s, 2H); 6.05 (broad s, 1H); 6.75 (dd, 1H); 7.30 (d, 2H); 7.55 (d, 2H); 7.75 (dd, 1H); 8.45 (dd, 1H).

EXAMPLE 6

Compound 63

2-(methylamino)-2-oxoethyl 4-[5-(2-methylpropyl)-2-pyridyl]-1-piperazinecarboxylate

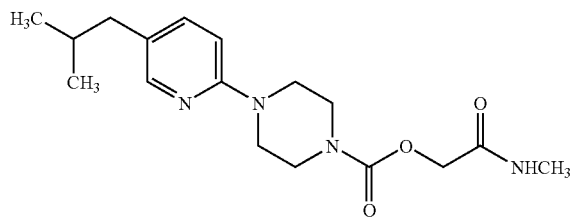

6.1. 2-(methylamino)-2-oxoethyl 4-(5-bromo-2-pyridyl)-1-piperazinecarboxylate The process is performed as described in Example 1 (step 1.4.). Starting with 2.20 g (5.91 mmol) of 2-(ethyloxy)-2-oxoethyl 4-(5-bromo-2-pyridyl)-1-piperazinecarboxylate, obtained in step 3.3. of Example 3, and 14.80 ml (29.55 mmol) of a solution of methylamine (2M) in tetrahydrofuran, and after crystallization from diisopropyl ether, 1.974 g of pure product are obtained in the form of a white solid.

6.2. 2-(methylamino)-2-oxoethyl 4-[5-(2-methylpropyl)-2-pyridyl]-1-piperazinecarboxylate 0.88 g (2.47 mmol) of 2-(methylamino)-2-oxoethyl 4-(5-bromo-2-pyridyl)-1-piperazinecarboxylate, obtained in step 6.1, 0.33 g (3.22 mmol) of isobutylboronic acid, 1.16 g (5.44 mmol) of hydrated potassium phosphate and 0.07 g (0.25 mmol) of tricyclohexylphosphine suspended in 11 ml of toluene are placed together under an inert atmosphere. 0.028 g (0.12 mmol) of palladium diacetate is then added. The reaction mixture is then refluxed for 3 hours. The mixture is allowed to cool to room temperature and 15 ml of water and 15 ml of ethyl acetate are then added. The salts are separated out by filtration through a sinter, the phases are separated by settling, the aqueous phase is extracted twice with ethyl acetate, and the combined organic phases are washed with saturated aqueous sodium chloride solution and dried over sodium sulfate. After evaporating off the solvent, the residue obtained is purified by chromatography on silica gel, eluting with a 97/3 mixture of dichloromethane and methanol. After crystallization from diisopropyl ether, 0.17 g of product is obtained in the form of a white solid.

LC-MS: M+H=335
m.p. (° C.): 127-129° C.
$^1$H NMR (CDCl$_3$) δ (ppm): 0.90 (d, 6H); 1.80 (m, 1H); 2.35 (d, 2H); 2.90 (d, 3H); 3.60 (m, 8H); 4.65 (s, 2H); 6.10 (broad s, 1H); 6.60 (d, 1H); 7.35 (dd, 1H); 8.0 (d, 1H).

EXAMPLE 7

Compound 85

2-(methylamino)-2-oxoethyl 4-{6-[3-(trifluoromethyl)phenyl]-3-pyridyl}-1-piperazinecarboxylate

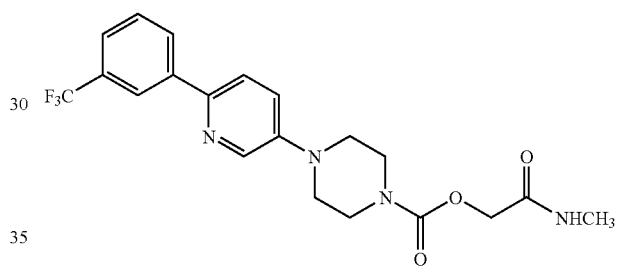

7.1. 1,1-dimethylethyl 4-(3-pyridyl)-1-piperazinecarboxylate 7.07 g (44.74 mmol) of 3-bromopyridine, 10 g (53.69 mmol) of 1,1-dimethylethyl 1-piperazinecarboxylate, 6.02 g (62.64 mmol) of sodium tert-butoxide and 0.836 g (1.34 mmol) of (2,2'-bis(diphenylphosphino)-1,1'-binaphthyl) (BINAP) suspended in 100 ml of toluene are introduced under an inert atmosphere. 0.41 g (0.45 mmol) of [tris(dibenzylideneacetone)dipalladium] (Pd$_2$(dba)$_3$) is then added. The reaction mixture is then refluxed for 22 hours. The mixture is allowed to cool to room temperature, the salts are separated out by filtration through glass fiber and the filtrate is then concentrated under reduced pressure. The residue is taken up in 100 ml of ethyl acetate and 100 ml of water, the aqueous phase is separated out and extracted several times with ethyl acetate, the combined organic phases are washed with saturated aqueous sodium chloride solution and dried over sodium sulfate, and the filtrate is concentrated under reduced pressure. The residue thus obtained is purified by chromatography on silica gel, eluting with a 98/2 and then 95/5 mixture of dichloromethane and methanol. 9.80 g of product are obtained in the form of an oil that crystallizes at room temperature.

7.2. 1,1-dimethylethyl 4-(6-bromo-3-pyridyl)-1-piperazinecarboxylate 2.70 g (15.19 mmol) of N-bromosuccinimide (NBS) are added portionwise to a solution of 4 g (15.19 mmol) of 1,1- dimethylethyl 4-(3-pyridyl)-1-piperazinecarboxylate, obtained in step 7.1, in 50 ml of acetonitrile, cooled to about 0° C. Stirring is continued at 0° C. for 15 minutes and then at room temperature for 2 hours. 100 ml of aqueous sodium hydroxide solution (1M) and 100 ml of ethyl acetate are added to the reaction medium. The aqueous phase is separated out and extracted twice with ethyl acetate, the combined organic phases are washed with saturated aqueous sodium chloride solution and dried over sodium sulfate, and the filtrate is concentrated under reduced pressure. 5.16 g of product are thus obtained in the form of an orange-yellow solid, and are used without further purification in the following step.

7.3. 1-(6-bromo-3-pyridyl)piperazine 11.20 ml (150.77 mmol) of trifluoroacetic acid are slowly added to a suspension of 5.16 g (15.08 mmol) of 1,1-dimethylethyl 4-(6-bromo-3-pyridyl)-1-piperazinecarboxylate, obtained in step 7.2, in 70 ml of dichloromethane. Stirring is continued at room temperature for 16 hours. The reaction mixture is concentrated under reduced pressure, the residue is taken up in 40 ml of chloroform and 4 ml of aqueous sodium hydroxide solution (10M) are then slowly added. The aqueous phase is separated out and then extracted twice with chloroform. The organic phases are combined and are washed with saturated aqueous sodium chloride solution. The organic phase is dried over sodium sulfate and the filtrate is concentrated under reduced pressure. 5.16 g of product are thus obtained in the form of an orange-colored oil that crystallizes at room temperature. This product is used without further purification in the following step.

7.4. 2-(ethyloxy)-2-oxoethyl 4-(6-bromo-3-pyridyl)-1-piperazinecarboxylate

The process is performed as described in Example 1 (step 1.2.). Starting with 3.57 g (14.76 mmol) of 1-(6-bromo-3-pyridyl)piperazine, obtained in step 7.3, and 3.97 g (17.71 mmol) of ethyl [(phenyloxycarbonyl)oxy]acetate, prepared in step 1.1. of Example 1, and after chromatography on silica gel, eluting with a 99/1 and then 98/2 mixture of dichloromethane and methanol, 3.75 g of product are obtained in the form of a yellow oil that crystallizes at room temperature.

7.5. 2-(ethyloxy)-2-oxoethyl 4-{6-[3-(trifluoromethyl)phenyl]-3-pyridyl}-1-piperazinecarboxylate The process is performed according to the procedure described in Example 1 (step 1.3.). Starting with 1.28 g (3.43 mmol) of 2-(ethyloxy)-2-oxoethyl 4-(6-bromo-3-pyridyl)-1-piperazinecarboxylate, obtained in step 7.4, 1.96 g (10.29 mmol) of 3-(trifluoromethyl)phenylboronic acid, 2.91 g (13.72 mmol) of hydrated potassium phosphate and 0.40 g (0.34 mmol) of tetrakis(triphenylphosphine)palladium, and after chromatography on silica gel, eluting with a mixture 35/65 of ethyl acetate and cyclohexane, 0.98 g of pure product is obtained in the form of an oil that crystallizes at room temperature.

7.6. 2-(methylamino)-2-oxoethyl 4-{6-[3-(trifluoromethyl)phenyl]-3-pyridyl}-1-piperazinecarboxylate The procedure described in Example 1 (step 1.4.) is used. Starting with 0.60 g (1.37 mmol) of 2-(ethyloxy)-2-oxoethyl 4-{6-[3-(trifluoromethyl)phenyl]-3-pyridyl}-1-piperazinecarboxylate, obtained in step 7.5, and 3.40 ml (6.86 mmol) of a solution of methylamine (2M) in tetrahydrofuran, and after chromatography on silica gel, eluting with a 98/2 and then 97/3 mixture of dichloromethane and methanol, followed by washing with diisopropyl ether, 0.36 g of pure product is obtained in the form of a white solid.

LC-MS: M+H=423
m.p. (° C.): 146-150° C.
$^1$H NMR (CDCl$_3$) δ (ppm): 2.90 (d, 3H); 3.35 (m, 4H); 3.80 (m, 4H); 4.65 (s, 2H); 6.05 (broad s, 1H); 7.30 (m, 1H); 7.65 (m, 2H); 7.70 (d, 1H); 8.10 (d, 1H); 8.25 (s, 1H); 8.45 (d, 1H).

EXAMPLE 8

Compound 86

2-amino-2-oxoethyl 4-{6-[3-(trifluoromethyl)phenyl]-3-pyridyl}-1-piperazinecarboxylate

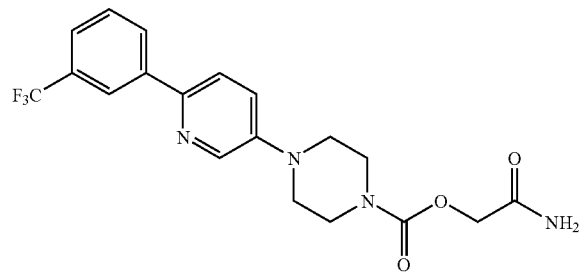

5.90 ml (41.40 mmol) of a solution of ammonia (7N) in methanol are added to a solution of 0.30 g (0.69 mmol) of 2-(ethyloxy)-2-oxoethyl 4-{6-[3-(trifluoromethyl)phenyl]-3-pyridyl}-1-piperazinecarboxylate, obtained in step 7.5. of Example 7, in 6 ml of a 1/1 mixture of methanol and tetrahydrofuran. Stirring is continued at room temperature for 22 hours. After concentrating under reduced pressure, the residue obtained is purified by chromatography on silica gel, eluting with a 96/4 mixture of dichloromethane and methanol, followed by washing with diisopropyl ether. 0.19 g of pure product is obtained in the form of a yellow solid.

LC-MS: M+H=409
m.p. (° C.): 155-157° C.
$^1$H NMR (CDCl$_3$) δ (ppm): 3.35 (m, 4H); 3.75 (m, 4H); 4.70 (s, 2H); 5.50 (broad s, 1H); 6.0 (broad s, 1H); 7.30 (m, 1H); 7.55 (m, 2H); 7.70 (d, 1H); 8.10 (d, 1H); 8.25 (s, 1H); 8.40 (d, 1H).

EXAMPLE 9

Compound 66

2-(methylamino)-2-oxoethyl 4-[6-(2-methylpropyl)-3-pyridyl]-1-piperazinecarboxylate

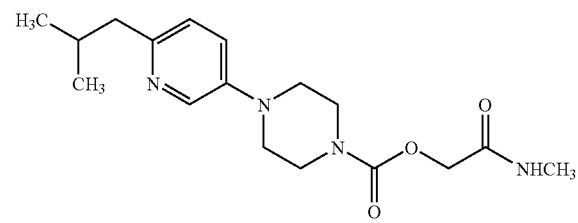

9.1. 2-(methylamino)-2-oxoethyl 4-(6-bromo-3-pyridyl)-1-piperazinecarboxylate The procedure described in Example 1 (step 1.4.) is used. Starting with 2.35 g (6.32 mmol) of 2-(ethyloxy)-2-oxoethyl 4-(6-bromo-3-pyridyl)-1-piperazinecarboxylate, obtained in step 7.4. of Example 7, and 15.80 ml (31.61 mmol) of a solution of methylamine (2M) in tetrahydrofuran, and after chromatography on silica gel, eluting with a 98/2 and then 97/3 mixture of dichloromethane and methanol, 1.779 g of product are obtained in the form of a white solid.

m.p. (° C.): 164° C.

9.2. 2-(methylamino)-2-oxoethyl 4-[6-(2-methylpropyl)-3-pyridyl]-1-piperazinecarboxylate 1.25 g (3.50 mmol) of 2-(methylamino)-2-oxoethyl 4-(6-bromo-3-pyridyl)-1-piperazinecarboxylate, prepared in step 9.1, and 0.12 g (0.17 mmol) of dichlorobis(triphenylphosphine)palladium (Pd(PPh$_3$)$_2$Cl$_2$) suspended in 7 ml of tetrahydrofuran are introduced under an inert atmosphere. 17.50 ml (8.74 mmol) of a solution of bromoisobutylzinc (0.5M) in tetrahydrofuran are then added. Stirring is continued at room temperature for 19 hours. The reaction mixture is poured into 25 ml of water and 25 ml of ethyl acetate. The insoluble material is filtered off through glass fiber. The phases are separated by settling, the aqueous phase is extracted twice with ethyl acetate, the combined organic phases are dried over sodium sulfate and the filtrate is concentrated under reduced pressure. The residue thus obtained is purified by chromatography on silica gel, eluting with a 95/5 mixture of dichloromethane and methanol, followed by crystallization from diisopropyl ether. 0.36 g of product is obtained in the form of a brown solid.

LC-MS: M+H=335
m.p. (° C.): 87-89° C.
$^1$H NMR (CDCl$_3$) δ (ppm): 0.90 (d, 6H); 2.05 (m, 1H); 2.60 (d, 2H); 2.90 (d, 3H); 3.20 (m, 4H); 3.70 (m, 4H); 4.65 (s, 2H); 6.05 (broad s, 1H); 7.0-7.20 (m, 2H); 8.25 (d, 1H).

EXAMPLE 10

Compound 87

2-(methylamino)-2-oxoethyl 4-{6-[3-(trifluoromethyl)phenyl]-3-pyridazinyl}-1-piperazinecarboxylate

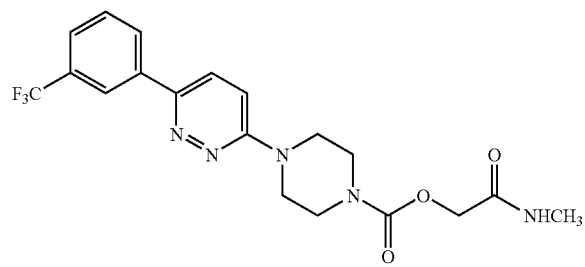

10.1. 2-(ethyloxy)-2-oxoethyl 4-(6-chloro-3-pyridazinyl)-1-piperazinecarboxylate The process is performed as described in Example 1 (step 1.2.). Starting with 1.60 g (8.05 mmol) of 3-chloro-6-(1-piperazinyl)pyridazine (J. Med. Chem., 18, 2002, 4011-4017) and 1.99 g (8.86 mmol) of ethyl [(phenyloxycarbonyl)oxy]acetate, prepared in step 1.1. of Example 1, and after chromatography on silica gel, eluting with a 98/2 mixture of dichloromethane and methanol, 1.70 g of product are obtained in the form of a white solid.

m.p. (° C.): 149-151° C.

10.2. 2-(ethyloxy)-2-oxoethyl 4-{6-[3-(trifluoromethyl)phenyl]-3-pyridazinyl}-1-piperazinecarboxylate The process is performed according to the procedure described in Example 1 (step 1.3.). Starting with 1.15 g (3.50 mmol) of 2-(ethyloxy)-2-oxoethyl 4-(6-chloro-3-pyridazinyl)-1-piperazinecarboxylate, obtained in step 10.1, 1.99 g (10.49 mmol) of 3-(trifluoromethyl)phenylboronic acid, 2.97 g (13.99 mmol) of hydrated potassium phosphate and 0.40 g (0.35 mmol) of tetrakis(triphenylphosphine)palladium, and after chromatography on silica gel, eluting with a 35/65 and then 45/55 mixture of ethyl acetate and cyclohexane, 0.67 g of pure product is obtained in the form of a solid.

m.p. (° C.): 126-128° C.

10.3. 2-(methylamino)-2-oxoethyl 4-{6-[3-(trifluoromethyl)phenyl]-3-pyridazinyl}-1-piperazinecarboxylate The procedure described in Example 1 (step 1.4.) is used. Starting with 0.66 g (1.51 mmol) of 2-(ethyloxy)-2-oxoethyl 4-{6-[3-(trifluoromethyl)phenyl]-3-pyridazinyl}-1-piperazinecarboxylate, obtained in step 10.2, and 3 ml (6.02 mmol) of a solution of methylamine (2M) in tetrahydrofuran, and after chromatography on silica gel, eluting with a 96/4 mixture of dichloromethane and methanol, followed by washing with diisopropyl ether, 0.50 g of product is obtained in the form of a white solid.

LC-MS: M+H=424
m.p. (° C.): 151-153° C.
$^1$H NMR (DMSO) δ (ppm): 2.60 (d, 3H); 3.55 (m, 4H); 3.75 (m, 4H); 4.45 (s, 2H); 7.40 (d, 1H); 7.80 (m, 3H); 8.10 (d, 1H); 8.35 (m, 2H).

EXAMPLE 11

Compound 103

2-(methylamino)-2-oxoethyl 4-(5-{4-[(trifluoromethyl)oxy]phenyl}-2-pyridyl)-1,4-diazepane-1-carboxylate

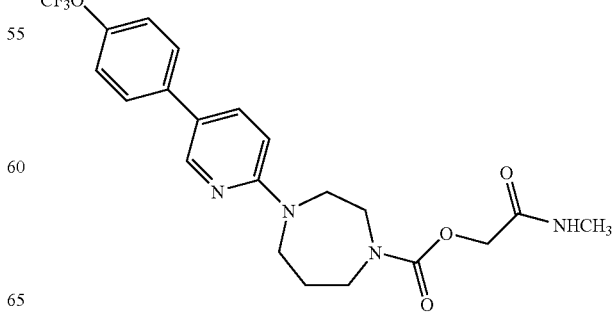

11.1. 1,1-dimethylethyl 4-(5-bromo-2-pyridyl)-1,4-diazepane-1-carboxylate 1.03 g (5 mmol) of 1,1-dimethylethyl 1,4-diazepane-1-carboxylate, 1.19 g (5 mmol) of 2,5-dibromopyridine and 0.7 g (5 mmol) of potassium carbonate suspended in 0.90 ml of dimethyl sulfoxide (DMSO) are introduced into an autoclave. The mixture is heated at 150° C. for 22 hours. The reaction mixture is allowed to cool to room temperature, it is taken up in ethyl acetate, and the organic solution is washed with water and then brine, and dried over sodium sulfate. The filtrate is concentrated under reduced pressure and the residue thus obtained is purified by chromatography on silica gel, eluting with a 99.5/0.5 mixture of dichloromethane and methanol. 1.63 g of product are obtained in the form of an oil, and are used without further purification in the following step.

11.2. 1-(5-bromo-2-pyridyl)-1,4-diazepane 6 ml of a solution of hydrogen chloride (6N) in isopropanol are added to a solution of 1.63 g (4.4 mmol) of 1,1-dimethylethyl 4-(5-bromo-2-pyridyl)-1,4-diazepane-1-carboxylate, obtained in step 11.1, in 12 ml of dioxane and 4 ml of ethanol. This reaction mixture is maintained at 70° C. for 3 hours. The mixture is allowed to cool to room temperature and is then concentrated under reduced pressure. 1.32 g of a white solid are obtained after crystallization from acetone. These crystals are taken up in 10 ml of dichloromethane and the reaction medium is basified to pH=14, by adding 28% ammonia solution. The organic phase is recovered by filtration through a hydrophobic cartridge and the filtrate is concentrated under reduced pressure. 0.96 g of product is obtained in the form of an oil, and is used without further purification in the following step.

11.3. 2-(methylamino)-2-oxoethyl 4-(5-bromo-2-pyridyl)-1,4-diazepane-1-carboxylate The process is performed as described in Example 1 (step 1.2.). Starting with 0.95 g (3.70 mmol) of 1-(5-bromo-2-pyridyl)-1,4-diazepane, obtained in step 11.2, and 0.94 g (3.70 mmol) of 2-(methylamino)-2-oxoethyl 4-nitrophenyl carbonate, prepared in step 2.2. of Example 2, and after chromatography on silica gel, eluting with a 30/70 mixture of ethyl acetate and cyclohexane and then with a 95/5 mixture of dichloromethane and methanol, followed by crystallization from diisopropyl ether, 0.97 g of product is obtained in the form of a white solid.

11.4. 2-(methylamino)-2-oxoethyl 4-(5-{4-[(trifluoromethyl)oxy]phenyl}-2-pyridyl)-1,4-diazepane-1-carboxylate 0.12 g (0.3 mmol) of 2-(methylamino)-2-oxoethyl 4-(5-bromo-2-pyridyl)-1,4-diazepane-1-carboxylate, prepared in step 11.3, 0.25 g (1.2 mmol) of 4-(trifluoromethoxy)phenylboronic acid and 0.9 ml (1.8 mmol) of aqueous sodium carbonate solution (2M), suspended in 3.5 ml of toluene and 0.8 ml of ethanol are introduced into a Pyrex reactor. 0.07 g (0.06 mmol) of tetrakis(triphenylphosphine)palladium is then added and, after sealing the reactor, it is maintained at 150° C. for 15 minutes under microwave irradiation. The organic phase is recovered after separation of the phases by settling, and the filtrate is concentrated under reduced pressure. The residue thus obtained is purified by chromatography on silica gel, eluting with a 30/70/5 mixture of ethyl acetate, cyclohexane and methanol. After crystallization from diisopropyl ether, 0.078 g of product is obtained in the form of a white solid.

LC-MS: M+H=452 m.p. (° C.): 191-193° C.

$^1$H NMR (DMSO) (ppm): 1.70-2.00 (m, 2H); 2.55 (d, 3H); 3.25-3.40 (m, 2H); 3.40-3.90 (m, 6H); 4.35 (d, 2H); 6.75 (d, 1H); 7.35 (d, 2H); 7.70 (broad d, 2H+NH); 7.80 (dd, 1H); 8.45 (d, 1H).

Table 1 below illustrates the chemical structures and the physical properties of a number of compounds according to the invention.

In the "base or salt" column, "base" represents a compound in free base form, whereas "HCl" represents a compound in hydrochloride form. In the table, OMe represents a methoxy group.

In the "m.p. (° C.) or M+H" column, m.p. (° C.) is the melting point of the compound in degrees Celsius and M+H is the value of the mass of the compound protonated with a hydrogen atom (mass of the compound+1), determined by LC-MS (Liquid Chromatography-Mass Spectroscopy).

TABLE 1

(I)

| No | $R_1$ | m | $R_2$ | Base or salt | m.p. (°C.) or M + H |
|---|---|---|---|---|---|
| 1 | phenyl | 1 | $CH_2CONHCH_3$ | base | 111-112 |
| 2. | 2-chlorophenyl | 1 | $CH_2CONHCH_3$ | base | 121-122 |

TABLE 1-continued (I)

| No | R₁ | m | R₂ | Base or salt | m.p. (°C.) or M + H |
|---|---|---|---|---|---|
| 3. | 3-Cl-phenyl | 1 | CH₂CONHCH₃ | base | 115-116 |
| 4. | 4-Cl-phenyl | 1 | CH₂CONHCH₃ | base | 154-155 |
| 5. | 2-F-phenyl | 1 | CH₂CONHCH₃ | base | 132-133 |
| 6. | 3-F-phenyl | 1 | CH₂CONHCH₃ | base | 132-133 |
| 7. | 4-F-phenyl | 1 | CH₂CONHCH₃ | base | 127-128 |
| 8. | 4-NC-phenyl | 1 | CH₂CONHCH₃ | base | 151-152 |
| 9. | 2-CH₃-phenyl | 1 | CH₂CONHCH₃ | base | 102-103 |
| 10. | 3-CH₃-phenyl | 1 | CH₂CONHCH₃ | base | 102-103 |
| 11. | 4-CH₃-phenyl | 1 | CH₂CONHCH₃ | base | 119-120 |
| 12. | 2-OMe-phenyl | 1 | CH₂CONHCH₃ | base | 119-120 |
| 13. | 3-OMe-phenyl | 1 | CH₂CONHCH₃ | base | 86-87 |

TABLE 1-continued
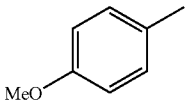
(I)
| No | R₁ | m | R₂ | Base or salt | m.p. (°C.) or M + H |
|---|---|---|---|---|---|
| 14. | 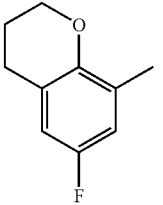 | 1 | CH₂CONHCH₃ | base | 121-122 |
| 15. | 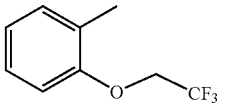 | 1 | CH₂CONHCH₃ | base | 189-190 |
| 16. | 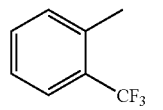 | 1 | CH₂CONHCH₃ | base | 113-114 |
| 17. | 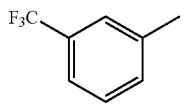 | 1 | CH₂CONHCH₃ | base | 91-93 |
| 18. | 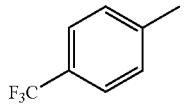 | 1 | CH₂CONHCH₃ | base | 124-125 |
| 19. |  | 1 | CH₂CONH₂ | base | M + H = 332 |
| 20. | 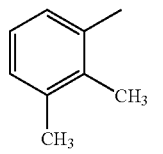 | 1 | CH₂CONHCH₃ | base | 171-172 |
| 21. | 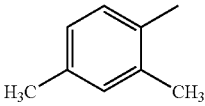 | 1 | CH₂CONHCH₃ | base | 110-111 |
| 22. | 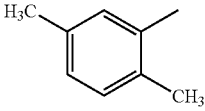 | 1 | CH₂CONHCH₃ | base | 125-126 |
| 23. | 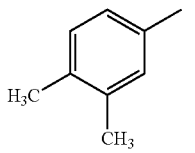 | 1 | CH₂CONHCH₃ | base | 121-122 |
| 24. | 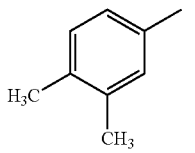 | 1 | CH₂CONHCH₃ | base | 121-122 |

TABLE 1-continued
(I)
| No | R₁ | m | R₂ | Base or salt | m.p. (°C.) or M + H |
|---|---|---|---|---|---|
| 25. | 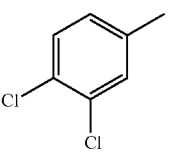 | 1 | CH₂CONHCH₃ | base | 108-109 |
| 26. | 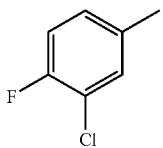 | 1 | CH₂CONHCH₃ | base | 123-124 |
| 27. | 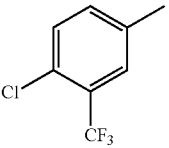 | 1 | CH₂CONHCH₃ | base | 148-149 |
| 28. | 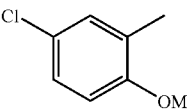 | 1 | CH₂CONHCH₃ | base | 165-166 |
| 29. | 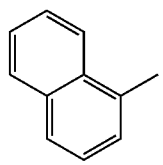 | 1 | CH₂CONHCH₃ | base | 117-118 |
| 30. | 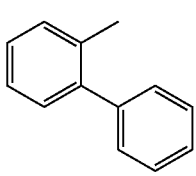 | 1 | CH₂CONHCH₃ | HCl | 172-174 |
| 31. | 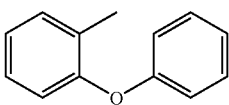 | 1 | CH₂CONHCH₃ | HCl | 103-104 |
| 32. | 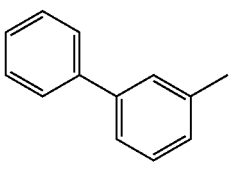 | 1 | CH₂CONHCH₃ | HCl | 199-200 |

TABLE 1-continued (I)

| No | R₁ | m | R₂ | Base or salt | m.p. (°C.) or M + H |
|---|---|---|---|---|---|
| 33. | 4-biphenyl | 1 | CH₂CONHCH₃ | base | 193-194 |
| 34. | 4'-chloro-4-biphenyl | 1 | CH₂CONHCH₃ | base | 180-181 |
| 35. | 4'-fluoro-4-biphenyl | 1 | CH₂CONHCH₃ | base | 175-176 |
| 36. | 4'-nitro-4-biphenyl | 1 | CH₂CONHCH₃ | base | 197-198 |
| 37. | 3'-trifluoromethyl-4-biphenyl | 1 | CH₂CONHCH₃ | base | 129-130 |
| 38. | 4'-trifluoromethyl-4-biphenyl | 1 | CH₂CONHCH₃ | base | 207-208 |
| 39. | 3'-isopropyl-4-biphenyl | 1 | CH₂CONHCH₃ | base | 123-124 |

TABLE 1-continued
(I)
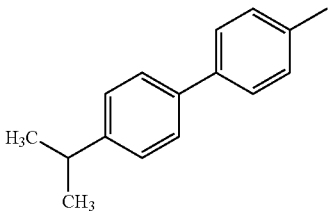
| No | R₁ | m | R₂ | Base or salt | m.p. (°C.) or M + H |
|---|---|---|---|---|---|
| 40. | 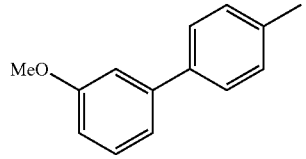 | 1 | CH₂CONHCH₃ | base | 202-203 |
| 41. | 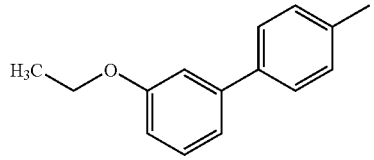 | 1 | CH₂CONHCH₃ | base | 157-158 |
| 42. | 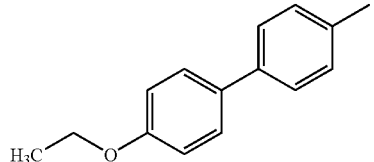 | 1 | CH₂CONHCH₃ | base | 139-140 |
| 43. | 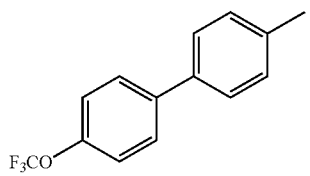 | 1 | CH₂CONHCH₃ | base | 215-216 |
| 44. | 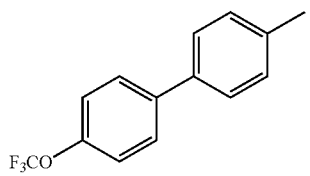 | 1 | CH₂CONHCH₃ | base | 187-189 |
| 45. |  | 1 | CH₂CONH₂ | base | 193-195 |
| 46. | 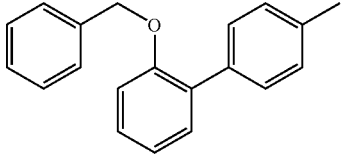 | 1 | CH₂CONHCH₃ | HCl | 199-200 |
| 47. | 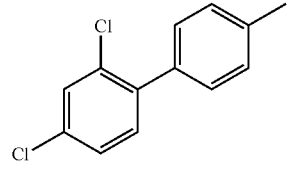 | 1 | CH₂CONHCH₃ | base | 181-182 |

TABLE 1-continued (I)

Structure: piperazine with N-C(=O)-O-R₂ on one nitrogen and R₁-(CH₂)ₘ- on the other nitrogen.

| No | R₁ | m | R₂ | Base or salt | m.p. (°C.) or M + H |
|---|---|---|---|---|---|
| 48. | 2-fluoro-3-methoxy-4'-biphenyl (MeO, F substituents) | 1 | CH₂CONHCH₃ | base | 164-165 |
| 49. | 3-fluoro-4-methoxy-4'-biphenyl (F, MeO substituents) | 1 | CH₂CONHCH₃ | base | 183-184 |
| 50. | 3-fluoro-4-benzyloxy-4'-biphenyl | 1 | CH₂CONHCH₃ | base | 180-181 |
| 51. | 2,5-dimethoxy-4'-biphenyl | 1 | CH₂CONHCH₃ | base | M + H = 414 |
| 52. | 2-methoxy-5-chloro-4'-biphenyl | 1 | CH₂CONHCH₃ | base | 132-133 |
| 53. | 3,4-methylenedioxy-4'-biphenyl | 1 | CH₂CONHCH₃ | base | 196 |

TABLE 1-continued (I)

| No | R₁ | m | R₂ | Base or salt | m.p. (°C.) or M + H |
|---|---|---|---|---|---|
| 54. | benzofuran-2-yl-phenyl | 1 | CH₂CONHCH₃ | base | 227-228 |
| 55. | naphthalen-1-yl-phenyl | 1 | CH₂CONHCH₃ | base | 188-189 |
| 56. | 4-methylnaphthalen-1-yl-phenyl | 1 | CH₂CONHCH₃ | base | 187-189 |
| 57. | naphthalen-2-yl-phenyl | 1 | CH₂CONHCH₃ | base | 194-195 |
| 58. | pyridin-2-yl | 1 | CH₂CONHCH₃ | base | 117-118 |
| 59. | pyridin-4-yl | 1 | CH₂CONHCH₃ | base | 164-165 |
| 60. | 5-methylpyridin-2-yl | 1 | CH₂CONHCH₃ | base | 138-140 |
| 61. |  |  | CH₂CONHCH₂CH₃ | base | 159-161 |
| 62. |  |  | CH₂CONHCH₂-cyclopropyl | base | 141-143 |
| 63. | 6-isobutylpyridin-3-yl | 1 | CH₂CONHCH₃ | base | 127-129 |
| 64. | 6-bromopyridin-3-yl | 1 | CH₂CONHCH₃ | base | 163-165 |

TABLE 1-continued (I)

| No | R₁ | m | R₂ | Base or salt | m.p. (°C.) or M + H |
|---|---|---|---|---|---|
| 65. | 5-methyl-2-propylpyridine | 1 | CH₂CONHCH₃ | base | 131-132 |
| 66. | 2-isobutyl-5-methylpyridine | 1 | CH₂CONHCH₃ | base | 87-89 |
| 67. | 3-methylpyrazine | 1 | CH₂CONHCH₃ | base | 152-154 |
| 68. | 3-methylpyrazine | | CH₂CONHCH₂CH₃ | base | 131-133 |
| 69. | 5-ethyl-2-methylpyrimidine | 1 | CH₂CONHCH₃ | base | 200-204 |
| 70. | 5-ethyl-2-methylpyrimidine | | CH₂CONHCH₂-cyclopropyl | base | 187-189 |
| 71. | 2-methyl-4-trifluoromethylpyrimidine | 1 | CH₂CONHCH₃ | base | 170-172 |
| 72. | 2-methyl-4-trifluoromethylpyrimidine | | CH₂CONHCH₂CH₃ | base | 146-148 |
| 73. | 6-methoxy-3-methylbenzisoxazole | 11 | CH₂CONHCH₃ | base | 191-192 |
| 74. | 4-methylthieno[3,2-c]pyridine | 1 | CH₂CONHCH₃ | base | 128-129 |
| 75. | 5-(4-chlorophenyl)-2-methylpyridine | 1 | CH₂CONHCH₃ | base | 203-206 |
| 76. | 2-methyl-5-(3-trifluoromethylphenyl)pyridine | 1 | CH₂CONHCH₃ | base | 158-160 |
| 77. | 2-methyl-5-(3-trifluoromethylphenyl)pyridine | 1 | CH₂CONH₂ | base | 186-188 |

TABLE 1-continued (I)

| No | R₁ | m | R₂ | Base or salt | m.p. (°C.) or M + H |
|---|---|---|---|---|---|
| 78. | 6-methyl-3-(4-trifluoromethylphenyl)pyridin-... | 1 | CH₂CONH₂ | base | 228-230 |
| 79. | | 1 | CH₂CONHCH₃ | base | 206-209 |
| 80. | | 1 | CH₂CONHCH₂CH₃ | base | 210-212 |
| 81. | | 1 | CH₂CONHCH₂-cyclopropyl | base | 198-200 |
| 82. | | 1 | CH(CH₃)CONHCH₃ | base | 198-200 |
| 83. | 6-methyl-3-(4-trifluoromethoxyphenyl)pyridin-... | 1 | CH₂CONHCH₃ | base | 188-190 |
| 84. | 3-(2,4-dichlorophenyl)-6-methylpyridin-... | 1 | CH₂CONHCH₃ | base | 185-187 |
| 85. | 5-methyl-2-(3-trifluoromethylphenyl)pyridin-... | 1 | CH₂CONHCH₃ | base | 146-150 |
| 86. | | 1 | CH₂CONH₂ | base | 155-157 |
| 87. | 6-methyl-3-(3-trifluoromethylphenyl)pyridazin-... | 1 | CH₂CONHCH₃ | base | 151-53 |
| 88. | 5-(3-chlorophenyl)-2-methylpyrimidin-... | 1 | CH₂CONHCH₃ | base | 198-202 |
| 89. | 2-methylquinolin-... | 1 | CH₂CONHCH₃ | base | 154-158 |
| 90. | 5-chloro-2-methylquinolin-... | 1 | CH₂CONH₂ | base | 208-210 |
| 91. | | 1 | CH₂CONHCH₃ | base | 190-191 |

TABLE 1-continued
(I)
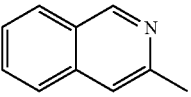
| No | R₁ | m | R₂ | Base or salt | m.p. (°C.) or M + H |
|---|---|---|---|---|---|
| 92. | 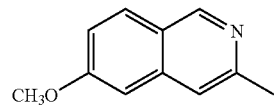 | 1 | CH₂CONH₂ | base | 188-190 |
| 93. | | 1 | CH₂CONHCH₃ | base | 166-168 |
| 94. | 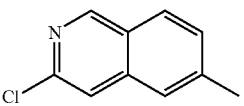 | 1 | CH₂CONHCH₃ | base | 181-183 |
| 95. | 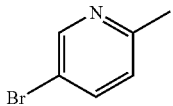 | 1 | CH₂CONH₂ | base | 218-220 |
| 96. | | 1 | CH₂CONHCH₃ | base | 188-190 |
| 97. | 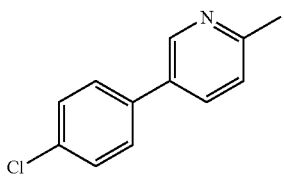 | 2 | CH₂CONHCH₃ | base | 156-158 |
| 98. | 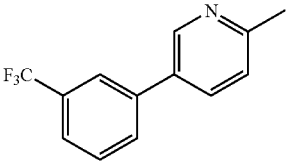 | 2 | CH₂CONHCH₃ | base | 204-206 |
| 99. | 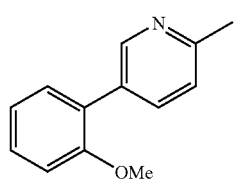 | 2 | CH₂CONHCH₃ | base | 174-176 |
| 100. | 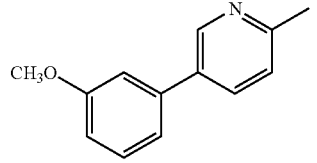 | 2 | CH₂CONHCH₃ | base | 109-111 |
| 101. | 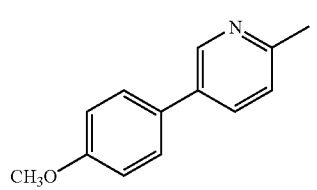 | 2 | CH₂CONHCH₃ | base | 124-126 |
| 102. | | 2 | CH₂CONHCH₃ | base | 155-157 |

TABLE 1-continued (I)

| No | R₁ | m | R₂ | Base or salt | m.p. (°C.) or M + H |
|---|---|---|---|---|---|
| 103. | (5-(4-trifluoromethoxyphenyl)pyridin-2-yl)methyl | 2 | $CH_2CONHCH_3$ | base | 191-193 |
| 104. | (5-(4-trifluoromethylphenyl)pyridin-2-yl)methyl | 2 | $CH_2CONHCH_3$ | base | M + H = 437 |
| 105. | (5-(2,4-dichlorophenyl)pyridin-2-yl)methyl | 2 | $CH_2CONHCH_3$ | base | 167-170 |
| 106. | 5-methyl-3-phenyl-1,2,4-thiadiazol-yl | 2 | $CH_2CONHCH_3$ | base | 124-126 |

The compounds of the invention were subjected to pharmacological tests to determine their inhibitory effect on the enzyme FAAH (Fatty Acid Amido Hydrolase).

The inhibitory activity was demonstrated in a radioenzymatic test based on measurement of the product of hydrolysis (ethanolamine [1-³H]) of anandamide [ethanolamine 1-³H] with FAAH (*Life Sciences* (1995), 56, 1999-2005 and *Journal of Pharmacology and Experimental Therapeutics* (1997), 283, 729-734). Thus, mouse brains (minus the cerebellum) are removed and stored at −80° C. The membrane homogenates are prepared extemporaneously by homogenizing the tissues with a Polytron machine in 10 mM Tris-HCl buffer (pH 8) containing 150 mM NaCl and 1 mM EDTA. The enzymatic reaction is then performed in 70 µl of buffer containing fatty-acid-free bovine serum albumin (1 mg/ml). The various test compounds at different concentrations, anandamide [ethanolamine 1-³H] (specific activity of 15-20 Ci/mmol) diluted to 10 µM with cold anandamide, and the membrane preparation (400 µg of thawed tissue per test) are successively added. After 15 minutes at 25° C., the enzymatic reaction is quenched by adding 140 µL of chloroform/methanol (2:1). The mixture is stirred for 10 minutes and then centrifuged for 15 minutes at 3500×g. An aliquot (30 µL) of the aqueous phase containing the ethanolamine [1-³H] is counted by liquid scintillation.

Under these conditions, the most active compounds of the invention have $IC_{50}$ values (concentration inhibiting 50% of the control enzymatic activity of FAAH) of between 0.001 and 1 µM.

Table 2 below presents the $IC_{50}$ values of a number of compounds according to the invention.

TABLE 2

| Compound No | $IC_{50}$ |
|---|---|
| 34 | 0.020 µM |
| 37 | 0.190 µM |
| 43 | 0.044 µM |
| 44 | 0.007 µM |
| 76 | 0.290 µM |
| 83 | 0.012 µM |

It is thus seen that the compounds according to the invention have inhibitory activity on the enzyme FAAH. The in vivo activity of the compounds of the invention was evaluated in a test of analgesia.

Thus, the intraperitoneal (i.p.) administration of PBQ (phenylbenzoquinone, 2 mg/kg in a 0.9% sodium chloride solution containing 5% ethanol) to male OF1 mice weighing 25 to 30 g causes abdominal stretching, on average 30 twists or contractions in the period from 5 to 15 minutes after injection. The test compounds are administered orally as a 0.5% suspension in Tween 80, 60 minutes or 120 minutes before the administration of PBQ. Under these conditions, the most powerful compounds of the invention reduce the number of stretches induced by PBQ by 35 to 70%, in a dosage range of between 1 and 30 mg/kg.

Table 3 below shows the results of the analgesia test for a number of compounds according to the invention.

TABLE 3

| Compound No | Reduction of the number of stretches (%) |
|---|---|
| 37 | −57 (a) |
| 44 | −53 (a) |
| 76 | −47 (a) |

(a) 1 mg/kg p.o. at 2 hours.

The enzyme FAAH (*Chemistry and Physics of Lipids*, (2000), 108, 107-121) catalyses the hydrolysis of the endogenous derivatives of amides and of esters of various fatty acids, such as N-arachidonoylethanolamine (anandamide), N-palmitoylethanolamine, N-oleoylethanolamine, oleamide or 2-arachidonoylglycerol. These derivatives exert various pharmacological activities by interacting, inter alia, with the cannabinoid and vanilloid receptors.

The compounds of the invention block this degradation pathway and increase the tissue content of these endogenous substances. They may be used in this respect in the prevention and treatment of pathologies in which the endogenous cannabinoids, and/or any other substrate metabolized by the enzyme FAAH, are involved. Mention may be made, for example, of the following diseases and complaints:
pain, especially acute or chronic pain of neurogenic type: migraine, neuropathic pain including the forms associated with herpes virus and diabetes; acute or chronic pain associated with inflammatory diseases: arthritis, rheumatoid arthritis, osteoarthritis, spondylitis, gout, vasculitis, Crohn's disease, irritable bowel syndrome; acute or chronic peripheral pain; vertigo; vomiting; nausea, in particular nausea following chemotherapy; eating disorders, in particular anorexia and cachexia of diverse nature; neurological and psychiatric pathologies: trembling, dyskinesia, dystonia, spasticity, compulsive and obsessive behavior, Tourette's syndrome, all forms of depression and anxiety of any nature or origin, mood disorders, psychosis; acute and chronic neurodegenerative diseases: Parkinson's disease, Alzheimer's disease, senile dementia, Huntington's chorea, lesions associated with cerebral ischaemia and with cranial and medullary trauma; epilepsy; sleeping disorders, including sleeping apnea; cardiovascular diseases, in particular hypertension, cardiac arrhythmia, arteriosclerosis, heart attack, cardiac ischaemia; renal ischaemia; cancers: benign skin tumors, papillomas and cerebral tumors, prostate tumors, cerebral tumors (glioblastomas, medullo-epitheliomas, medulloblastomas, neuroblastomas, tumors of embryonic origin, astrocytomas, astroblastomas, ependyomas, oligodendrogliomas, plexus tumor, neuroepitheliomas, tumor of the pineal gland, ependymoblastomas, malignant meningiomas, sarcomatoses, malignant melanomas, schwennomas); disorders of the immune system, especially autoimmune diseases: psoriasis, lupus erythematosus, connective tissue diseases, Sjögrer's syndrome, ankylosing spondylarthritis, undifferentiated spondylarthritis, Behcet's disease, haemolytic autoimmune anaemias, multiple sclerosis, amyotrophic lateral sclerosis, amylosis, graft rejection, diseases affecting the plasmocytic line; allergic diseases: immediate or delayed hypersensitivity, allergic rhinitis or conjunctivitis, contact dermatitis; parasitic, viral or bacterial infectious diseases: AIDS, meningitis; inflammatory diseases, especially articular diseases: arthritis, rheumatoid arthritis, osteoarthritis, spondylitis, gout, vascularitis, Crohn's disease, irritable bowel syndrome; osteoporosis; ocular complaints: ocular hypertension, glaucoma; pulmonary diseases: diseases of the respiratory pathways, bronchospasms, coughing, asthma, chronic bronchitis, chronic obstruction of the respiratory pathways, emphysema; gastrointestinal diseases: irritable bowel syndrome, intestinal inflammatory disorders, ulcers, diarrhea; urinary incontinence and inflammation of the bladder.

The use of the compounds according to the invention, in the form of base, of pharmaceutically acceptable acid-addition salt, of hydrate or of solvate, for the preparation of a medicament for treating the pathologies mentioned above forms an integral part of the invention.

A subject of the invention is also medicaments comprising a compound of formula (I), or a pharmaceutically acceptable acid-addition salt, or alternatively a hydrate or solvate of the compound of formula (I). These medicaments find their use in therapy, especially in the treatment of the pathologies mentioned above.

According to another of its aspects, the present invention relates to pharmaceutical compositions containing, as active principle, at least one compound according to the invention. These pharmaceutical compositions contain an effective dose of a compound according to the invention, or a pharmaceutically acceptable acid-addition salt, or a hydrate, or a solvate, of the said compound, and optionally one or more pharmaceutically acceptable excipients.

The said excipients are chosen, according to the pharmaceutical form and the desired mode of administration, from the usual excipients that are known to those skilled in the art.

In the pharmaceutical compositions of the present invention for oral, sublingual, subcutaneous, intramuscular, intravenous, topical, local, intrathecal, intranasal, transdermal, pulmonary, ocular or rectal administration, the active principle of formula (I) above, or the possible acid-addition salt thereof, or possible solvate or hydrate, may be administered in a unit administration form, as a mixture with standard pharmaceutical excipients, to animals and to human beings for the prophylaxis or treatment of the above disorders or diseases.

The appropriate unit administration forms comprise the oral forms such as tablets, soft or hard gel capsules, powders, granules, chewing gums and oral solutions or suspensions, sublingual, buccal, intratracheal, intraocular or intranasal administration forms, the forms for administration by inhalation, the subcutaneous, intramuscular or intravenous administration forms and the rectal or vaginal administration forms. For topical application, the compounds according to the invention may be used in creams, ointments or lotions.

By way of example, a unit administration form of a compound according to the invention in the form of a tablet may comprise the following components:

| | |
|---|---|
| Compound according to the invention | 50.0 mg |
| Mannitol | 223.75 mg |
| Sodium croscarmellose | 6.0 mg |
| Maize starch | 15.0 mg |
| Hydroxypropylmethylcellulose | 2.25 mg |
| Magnesium stearate | 3.0 mg |

The said unit forms are dosed to allow a daily administration of from 0.01 to 20 mg of active principle per kg of body weight, according to the galenical form.

There may be particular cases in which higher or lower doses are appropriate, and such doses are also included in the invention. According to the usual practice, the dosage that is appropriate for each patient is determined by the doctor according to the mode of administration, and the weight and response of the said patient.

According to another of its aspects, the invention also relates to a method for treating the pathologies indicated above, which comprises the administration of an effective dose of a compound according to the invention, an addition salt thereof with a pharmaceutically acceptable acid, a solvate or a hydrate of the said compound.

What is claimed is:

1. A compound of the formula (I):

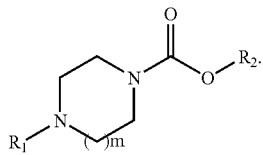

wherein m represents an integer equal to 2;

$R_1$ represents a group chosen from phenyl, pyridyl, pyridazinyl, pyrimidinyl, pyrazinyl, triazinyl, oxazolyl, thiazolyl, imidazolyl, oxadiazolyl, thiadiazolyl, triazolyl, naphthyl, quinolyl, tetrahydroquinolyl, isoquinolyl, tetrahydroisoquinolyl, phthalazinyl, quinazolinyl, quinoxalinyl, cinnolinyl, naphthyridinyl, benzofuryl, dihydrobenzofuryl, benzothienyl, dihydrobenzothienyl, indolyl, benzoxazolyl, benzisoxazolyl, benzothiazolyl, benzisothiazolyl, benzimidazolyl, indazolyl, pyrrolopyridyl, furopyridyl, dihydrofuropyridyl, thienopyridyl, dihydrothienopyridyl, imidazopyridyl, imidazopyrimidinyl, pyrazolopyridyl, oxazolopyridyl, isoxazolopyridyl, thiazolopyridyl or isothiazolopyridyl; wherein said group is optionally substituted with one or more groups $R_3$, which may be identical or different, or with a group $R_4$;

$R_2$ represents a group of formula $CHR_5CONHR_6$;

$R_3$ represents a halogen atom or a hydroxyl, cyano, nitro, $C_{1-6}$-alkyl, $C_{1-6}$-alkoxy, $C_{1-6}$-thioalkyl, $C_{1-6}$-fluoroalkyl, $C_{1-6}$-fluoroalkoxy, —O—($C_{2-3}$-alkylene)-, —O—($C_{1-3}$-alkylene)-O—, $C_{1-6}$-fluorothioalkyl, $C_{3-7}$-cycloalkyl, $C_{3-7}$-cycloalkyl-$C_{1-3}$-alkylene, piperidyl, benzyloxy, piperazinyl, pyrrolidinyl, morpholinyl, phenyloxy, $NR_7R_8$, $NHCOR_7$, $NHSO_2R_7$, $COR_7$, $CO_2R_7$, $CONR_7R_8$, $SO_2R_7$ or $SO_2NR_7R_8$ group;

$R_4$ represents a group chosen from phenyl, benzofuryl, naphthyl, pyridyl, pyrimidinyl, pyridazinyl, pyrazinyl, triazinyl, oxazolyl, thiazolyl, imidazolyl, oxadiazolyl, thiadiazolyl, triazolyl, quinolyl, tetrahydroquinolyl, isoquinolyl, tetrahydroisoquinolyl, phthalazinyl, quinazolinyl, quinoxalinyl, naphthyridinyl, cinnolinyl, benzothienyl, indolyl, benzoxazolyl, benzisoxazolyl, benzothiazolyl, benzisothiazolyl, benzimidazolyl, indazolyl, pyrrolopyridyl, furopyridyl, dihydrofuropyridyl, thienopyridyl, dihydrothienopyridyl, imidazopyridyl, imidazopyrimidinyl, pyrazopyridyl, oxazolopyridyl, isoxazolopyridyl, thiazolopyridyl or isothiazolo-pyridyl; wherein said group $R_4$ is optionally substituted with one or more groups $R_3$, which may be identical or different;

$R_5$ represents a hydrogen atom or a $C_{1-3}$-alkyl group;

$R_6$ represents a hydrogen atom or a $C_{1-6}$-alkyl, $C_{3-7}$-cycloalkyl or $C_{3-7}$-cycloalkyl-$C_{1-3}$-alkylene group; and $R_7$ and $R_8$ represent, independently of each other, a hydrogen atom, a $C_{1-3}$-alkyl group or a phenyl group; or a salt thereof.

2. The compound of formula (I) according to claim 1, wherein:

$R_1$ represents a group chosen from phenyl, pyridyl, pyrimidinyl, pyrazinyl, naphthyl, quinolyl, isoquinolyl, benzisoxazolyl or thienopyridyl; wherein said group is optionally substituted with one or more groups $R_3$, which may be identical or different;

$R_2$ represents a group of formula $CHR_5CONHR_6$;

$R_3$ represents a halogen atom or a cyano, $C_{1-6}$-alkyl, $C_{1-6}$-alkoxy, $C_{1-6}$-fluoroalkyl, $C_{1-6}$-fluoroalkoxy, —O—($C_{2-3}$-alkylene)- or phenyloxy group;

$R_5$ represents a hydrogen atom; and $R_6$ represents a hydrogen atom or a $C_{1-6}$-alkyl group.

3. The compound of formula (I) according to claim 1, wherein:

$R_1$ represents a group chosen from pyridyl, pyrimidinyl, pyrazinyl, quinolyl or isoquinolyl; wherein said group is optionally substituted with a group $R_3$;

$R_2$ represents a group of formula $CHR_5CONHR_6$;

$R_3$ represents a halogen atom, or a $C_{1-6}$-alkyl, $C_{1-6}$-alkoxy or $C_{1-6}$-fluoroalkyl group;

$R_5$ represents a hydrogen atom; and $R_6$ represents a hydrogen atom or a $C_{1-6}$-alkyl group.

4. The compound of formula (I) according to claim 1, wherein:

$R_1$ represents a group chosen from phenyl, pyridyl, pyridazinyl, pyrimidinyl or thiadiazolyl; wherein said group is optionally substituted with a group $R_4$;

$R_4$ represents a group chosen from phenyl, benzofuryl or naphthyl; wherein said group $R_4$ is optionally substituted with one or more groups $R_3$, which may be identical or different;

$R_2$ represents a group of formula $CHR_5CONHR_6$;

$R_3$ represents a halogen atom or a nitro, $C_{1-6}$-alkyl, $C_{1-6}$-alkoxy, $C_{1-6}$-fluoroalkyl, $C_{1-6}$-fluoroalkoxy, —O—($C_{1-3}$-alkylene)-O— or benzyloxy group;

$R_5$ represents a hydrogen atom; and $R_6$ represents a hydrogen atom or a $C_{1-6}$-alkyl or $C_{3-7}$-cycloalkyl-$C_{1-3}$-alkylene group.

5. The compound of formula (I) according to claim 1, wherein $R_1$ represents a group chosen from phenyl, pyridyl, pyridazinyl or pyrimidinyl;

wherein said group is optionally substituted with a group $R_4$;

$R_4$ represents a group chosen from phenyl, benzofuryl and naphthyl; wherein said group $R_4$ is optionally substituted with one or more groups $R_3$, which may be identical or different;

$R_2$ represents a group of formula $CHR_5CONHR_6$;

$R_3$ represents a halogen atom or a nitro, $C_{1-6}$-alkyl, $C_{1-6}$-alkoxy, $C_{1-6}$-fluoroalkyl, $C_{1-6}$-fluoroalkoxy, —O—($C_{1-3}$-alkylene)-O— or benzyloxy group;

$R_5$ represents a hydrogen atom; and $R_6$ represents a hydrogen atom or a $C_{1-6}$-alkyl group.

6. A process for preparing a compound of formula (I) according to claim 1, comprising the step of:
reacting an amine of formula (II):

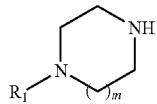

in which $R_1$ and m are as defined in the formula (I) according to claim 1, with a carbonate of formula (III):

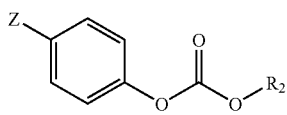

in which z represents a hydrogen atom or a nitro group and $R_2$ is as defined in the formula (I) according to claim 1.

7. A process for preparing a compound of formula (I) according to claim 1, comprising the step of:
converting the carbamate-ester of formula (Ia):

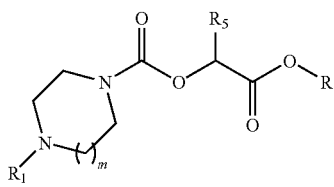

in which m, $R_1$ and $R_5$ are as defined in the formula (I) according to claim 1 and R represents a methyl or ethyl group,
via aminolysis using an amine of formula $R_6NH_2$ in which $R_6$ is as defined in the formula (I) according to claim 1.

8. A compound of the formula (Ia):

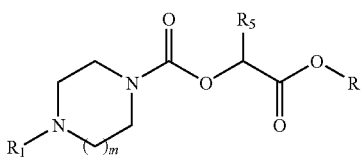

wherein
m represents an integer equal to 2;
R represents a methyl or ethyl group;
$R_1$ represents a group chosen from phenyl, pyridyl, pyridazinyl, pyrimidinyl, pyrazinyl, triazinyl, oxazolyl, thiazolyl, imidazolyl, oxadiazolyl, thiadiazolyl, triazolyl, naphthyl, quinolyl, tetrahydroquinolyl, isoquinolyl, tetrahydroisoquinolyl, phthalazinyl, quinazolinyl, quinoxalinyl, cinnolinyl, naphthyridinyl, benzofuryl, dihydrobenzofuryl, benzothienyl, dihydrobenzothienyl, indolyl, benzoxazolyl, benzisoxazolyl, benzothiazolyl, benzisothiazolyl, benzimidazolyl, indazolyl, pyrrolopyridyl, furopyridyl, dihydrofuropyridyl, thienopyridyl, dihydrothienopyridyl, imidazopyridyl, imidazopyrimidinyl, pyrazolopyridyl, oxazolopyridyl, isoxazolopyridyl, thiazolopyridyl or isothiazolopyridyl; wherein said group is optionally substituted with one or more groups $R_3$, which may be identical or different, or with a group $R_4$;

$R_3$ represents a halogen atom or a hydroxyl, cyano, nitro, $C_{1-6}$-alkyl, $C_{1-6}$-alkoxy, $C_{1-6}$-thioalkyl, $C_{1-6}$-fluoroalkyl, $C_{1-6}$-fluoroalkoxy, —O—($C_{2-3}$-alkylene), —O—($C_{1-3}$-alkylene)-O—, $C_{1-6}$-fluorothioalkyl, $C_{3-7}$-cycloalkyl, $C_{3-7}$-cycloalkyl-$C_{1-3}$-alkylene, piperidyl, benzyloxy, piperazinyl, pyrrolidinyl, morpholinyl, phenyloxy, $NR_7R_8$, $NHCOR_7$, $NHSO_2R_7$, $COR_7$, $CO_2R_7$, $CONR_7R_8$, $SO_2R_7$ or $SO_2NR_7R_8$ group;

$R_4$ represents a group chosen from phenyl, benzofuryl, naphthyl, pyridyl, pyrimidinyl, pyridazinyl, pyrazinyl, triazinyl, oxazolyl, thiazolyl, imidazolyl, oxadiazolyl, thiadiazolyl, triazolyl, quinolyl, tetrahydroquinolyl, isoquinolyl, tetrahydroisoquinolyl, phthalazinyl, quinazolinyl, quinoxalinyl, naphthyridinyl, cinnolinyl, benzothienyl, indolyl, benzoxazolyl, benzisoxazolyl, benzothiazolyl, benzisothiazolyl, benzimidazolyl, indazolyl, pyrrolopyridyl, furopyridyl, dihydrofuropyridyl, thienopyridyl, dihydrothienopyridyl, imidazopyridyl, imidazopyrimidinyl, pyrazopyridyl, oxazolopyridyl, isoxazolopyridyl, thiazolopyridyl or isothiazolo-pyridyl; wherein said group $R_4$ is optionally substituted with one or more groups $R_3$, which may be identical or different;

$R_5$ represents a hydrogen atom or a $C_{1-3}$-alkyl group; and $R_7$ and $R_8$ represent, independently of each other, a hydrogen atom, a $C_{1-3}$-alkyl group or a phenyl group.

9. A pharmaceutical composition comprising at least one compound of formula (I) according to claim 1 or a pharmaceutically acceptable salt thereof in combination with one or more pharmaceutically acceptable excipients.

10. A method of treating a disease selected from the group consisting of acute or chronic pain, vertigo, vomiting, nausea, eating disorder, sleeping disorder and renal ischaemia, comprising administering to a patient in need of said treatment a therapeutically effective amount of a compound of formula (I) according to claim 1, or a pharmaceutically acceptable salt thereof.

11. A method of treating a disease selected from the group consisting of acute or chronic pain, vertigo and sleeping disorder, comprising administering to a patient in need of said treatment a therapeutically effective amount of a compound of formula (I) according to claim 1, or a pharmaceutically acceptable salt thereof.

12. A method of treating a disease selected from the group consisting of hypertension, cardiac arrhythmia, arteriosclerosis, heart attack, cardiac ischaemia and renal ischaemia comprising administering to a patient in need of said treatment a therapeutically effective amount of a compound of formula (I) according to claim 1, or a pharmaceutically acceptable salt thereof.

13. A method of treating a disease selected from the group consisting of trembling, dyskinesia, dystonia, spasticity, compulsive and obsessive behavior and Tourette's syndrome comprising administering to a patient in need of said treatment a therapeutically effective amount of a compound of formula (I) according to claim 1, or a pharmaceutically acceptable salt thereof.

14. A method of treating a disease selected from the group consisting of depression, anxiety, mood disorder and psychosis comprising administering to a patient in need of said treatment a therapeutically effective amount of a compound of formula (I) according to claim 1, or a pharmaceutically acceptable salt thereof.

15. A method of treating a disease selected from the group consisting of Parkinson's disease, Alzheimer's disease, senile dementia, Huntington's chorea and lesions associated with cerebral ischaemia and with cranial and medullary trauma comprising administering to a patient in need of said treatment a therapeutically effective amount of a compound of formula (I) according to claim 1, or a pharmaceutically acceptable salt thereof.

16. A method of treating a disease selected from the group consisting of benign skin tumor, papillomas and cerebral tumor, prostate tumor, glioblastomas, medulloepitheliomas, medulloblastomas, neuroblastomas, tumors of embryonic origin, astrocytomas, astroblastomas, ependyomas, oligodendrogliomas, plexus tumor, neuroepitheliomas, tumor of the pineal gland, ependymoblastomas, malignant meningiomas, sarcomatoses, malignant melanomas and schwannomas comprising administering to a patient in need of said treatment a therapeutically effective amount of a compound of formula (I) according to claim 1, or a pharmaceutically acceptable salt thereof.

17. A method of treating a disease selected from the group consisting of psoriasis, lupus erythematosus, connective tissue diseases, Sjogrer's syndrome, ankylosing spondylarthritis, undifferentiated spondylarthritis, Behcet's disease, haemolytic autoimmune anaemias, multiple sclerosis, amyotrophic lateral sclerosis, amylosis, graft rejection and diseases affecting the plasmocytic line comprising administering to a patient in need of said treatment a therapeutically effective amount of a compound of formula (I) according to claim 1, or a pharmaceutically acceptable salt thereof.

18. A method of treating a disease selected from the group consisting of immediate or delayed hypersensitivity, allergic rhinitis or conjunctivitis and contact dermatitis comprising administering to a patient in need of said treatment a therapeutically effective amount of a compound of formula (I) according to claim 1, or a pharmaceutically acceptable salt thereof.

* * * * *

UNITED STATES PATENT AND TRADEMARK OFFICE
CERTIFICATE OF CORRECTION

PATENT NO. : 8,114,866 B2
APPLICATION NO. : 12/701897
DATED : February 14, 2012
INVENTOR(S) : Ahmed Abouabdellah et al.

It is certified that error appears in the above-identified patent and that said Letters Patent is hereby corrected as shown below:

On the title page, in item (57), in column 2, in "Abstract", in structure, line 3, delete

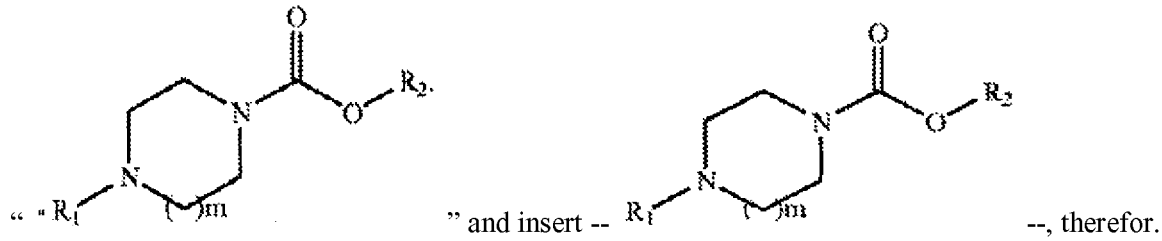

" and insert -- -- , therefor.

In the Specification:

In column 1, line 45, delete "triazolyl," and insert -- thiazolyl, --, therefor.

In column 6, line 10, delete "biphenyl}" and insert -- biphenylyl} --, therefor.

In column 35-36, in Table 1, line 13, delete "11" and insert -- 1 --, therefor.

In column 37-38, in Table 1, line 14, delete "151-53" and insert -- 151-153 --, therefor.

In column 41-42, in Table 1, line 7, delete "$CH_2CONHCH_3$" and insert -- $CH_2CONHCH_2CH_3$ --, therefor.

In column 43, line 59, delete "ependyomas," and insert -- ependymomas, --, therefor.

In column 43, line 62, delete "schwennomas);" and insert -- schwannomas); --, therefor.

In column 43, line 64, delete "Sjögrer's" and insert -- Sjögren's --, therefor.

In column 44, line 1, delete "plasmocytic" and insert -- plasmacytic --, therefor.

Signed and Sealed this
Twenty-sixth Day of November, 2013

Margaret A. Focarino
*Commissioner for Patents of the United States Patent and Trademark Office*

In column 44, line 6-7, delete "vascularitis," and insert -- vasculitis, --, therefor.

In the Claims:

In column 45, line 21-27, in claim 1, delete " 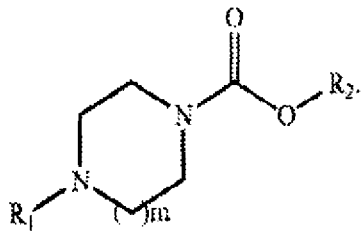 " and insert -- 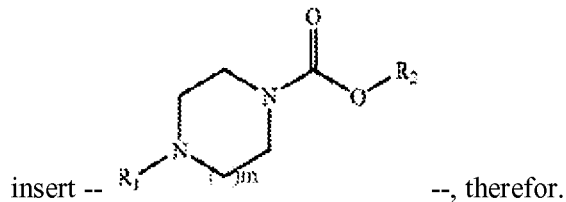 --, therefor.

In column 49, line 17, in claim 16, delete "ependyomas," and insert -- ependymomas, --, therefor.

In column 50, line 6, in claim 17, delete "Sjögrer's" and insert -- Sjögren's --, therefor.

In column 50, line 10, in claim 17, delete "plasmocytic" and insert -- plasmacytic --, therefor.